United States Patent
Schreuder et al.

(10) Patent No.: US 10,180,390 B2
(45) Date of Patent: Jan. 15, 2019

(54) FLOW CYTOMETRY SYSTEM AND METHOD

(71) Applicant: LIONIX INTERNATIONAL BV, Enschede (NL)

(72) Inventors: Frederik Schreuder, Rijssen (NL); Marcel Hoekman, Enschede (NL); Ronald Dekker, Enschede (NL); Seyed Naser Hosseini, Enschede (NL)

(73) Assignee: LioniX International BV, Enschede (NL)

( * ) Notice: Subject to any disclaimer, the term of this patent is extended or adjusted under 35 U.S.C. 154(b) by 118 days.

(21) Appl. No.: 15/163,556

(22) Filed: May 24, 2016

(65) Prior Publication Data

US 2016/0266029 A1    Sep. 15, 2016

Related U.S. Application Data

(63) Continuation of application No. 14/321,138, filed on Jul. 1, 2014, now Pat. No. 9,453,791.

(51) Int. Cl.
*G01N 15/14* (2006.01)
*G01N 21/05* (2006.01)
(Continued)

(52) U.S. Cl.
CPC ..... *G01N 15/1484* (2013.01); *G01N 15/1425* (2013.01); *G01N 15/1436* (2013.01);
(Continued)

(58) Field of Classification Search
CPC ........ G01N 21/00; G01N 21/64; G01N 15/10; G01N 15/1484; G01N 15/1436; G01N 15/1477; G01N 15/1454
See application file for complete search history.

(56) References Cited

U.S. PATENT DOCUMENTS 4,810,658 A * 3/1989 Shanks .................. G01N 21/03
                                                            250/227.31
4,945,245 A * 7/1990 Levin .................... G01N 21/648
                                                            250/458.1
(Continued)

FOREIGN PATENT DOCUMENTS

WO           8505680 A1   12/1985
WO        2010099118 A1    9/2010
WO     WO 2010099118 A1 *  9/2010  ......... G01N 15/1436

OTHER PUBLICATIONS

"International Search Report and Written Opinion", issued in International Application No. PCT/EP2015/065028, dated Sep. 15, 2015, Publisher: ISA / EPO.
(Continued)

*Primary Examiner* — David Porta
*Assistant Examiner* — Djura Malevic
(74) *Attorney, Agent, or Firm* — Kaplan Breyer Schwarz, LLP

(57) ABSTRACT

A flow cytometry system having a flow channel defined through the thickness of a substrate is disclosed. Fluid flowing through the flow channel is illuminated by a first plurality of surface waveguides that are arranged around the flow channel in a first plane, while a second plurality of surface waveguides arranged around the flow channel in a second plane receive light after it has interacted with the fluid. The illumination pattern provided to the fluid is controlled by controlling the phase of the light in the first plurality of surface waveguides. As a result, the fluid is illuminated with light that is uniform and has a low coefficient of variation, improving the ability to distinguish and quantify characteristics of the fluid, such as cell count, DNA content, and the like.

29 Claims, 16 Drawing Sheets

(51) Int. Cl.
*G01S 17/88* (2006.01)
*G01N 33/483* (2006.01)
*G01N 21/03* (2006.01)
*G01N 21/47* (2006.01)
*G01N 21/64* (2006.01)
*G01N 15/00* (2006.01)

(52) U.S. Cl.
CPC ......... *G01N 15/1459* (2013.01); *G01N 21/05* (2013.01); *G01N 33/483* (2013.01); *G01S 17/88* (2013.01); *B01L 2300/0654* (2013.01); *G01N 2015/0065* (2013.01); *G01N 2015/145* (2013.01); *G01N 2015/1454* (2013.01); *G01N 2021/0346* (2013.01); *G01N 2021/4742* (2013.01); *G01N 2021/6484* (2013.01); *G01N 2201/08* (2013.01)

(56) References Cited

U.S. PATENT DOCUMENTS

| | | | | |
|---|---|---|---|---|
| 5,166,515 | A * | 11/1992 | Attridge | G01N 21/6428 250/227.25 |
| 6,239,876 | B1 * | 5/2001 | Brandenberg | G01N 21/45 356/481 |
| 6,438,279 | B1 * | 8/2002 | Craighead | G02B 6/136 356/246 |
| 7,619,739 | B1 * | 11/2009 | Sutherland | G01N 21/774 356/432 |
| 7,920,267 | B2 * | 4/2011 | Cho | G01N 21/553 356/317 |
| 8,279,445 | B2 * | 10/2012 | Dominguez Horna | G01N 21/45 356/477 |
| 8,325,347 | B2 * | 12/2012 | Cottier | G01N 21/45 356/477 |
| 8,536,542 | B2 * | 9/2013 | Fortin | G01N 15/1436 250/458.1 |
| 8,928,875 | B2 * | 1/2015 | Braeckmans | G01N 21/6458 356/246 |
| 2003/0060695 | A1 * | 3/2003 | Connelly | A61B 5/14532 600/365 |
| 2004/0081384 | A1 * | 4/2004 | Datesman | G01N 21/431 385/12 |
| 2005/0151097 | A1 | 7/2005 | Arnold et al. | |
| 2006/0251371 | A1 * | 11/2006 | Schmidt | G01N 21/0303 385/129 |
| 2010/0084570 | A1 * | 4/2010 | Katagiri | G02F 1/025 250/458.1 |
| 2010/0208256 | A1 * | 8/2010 | Tang | G01N 21/0303 356/326 |
| 2011/0291025 | A1 | 12/2011 | Fortin et al. | |
| 2012/0077190 | A1 * | 3/2012 | Lundquist | G01N 21/6452 435/6.1 |
| 2012/0293797 | A1 * | 11/2012 | Braeckmans | G01N 21/05 356/246 |

OTHER PUBLICATIONS

Dubeau-Laramee, et al., "Microflow1, a sheathless fiber-optic flow cytometry biomedical platform: demonstration onboard the international space station", "Cytometry Part A; XP055211830; issn: 1552-4922, DOI: 10.1002/cyto. a.22427", Dec. 12, 2013, pp. 322-331, vol. 85, No. 4, Publisher: International Society for Advancement of Cytometry.

Office Action issued in parent U.S. Appl. No. 14/321,138, dated Jan. 21, 2016, Publisher: USPTO, Country of Publication: US.

* cited by examiner

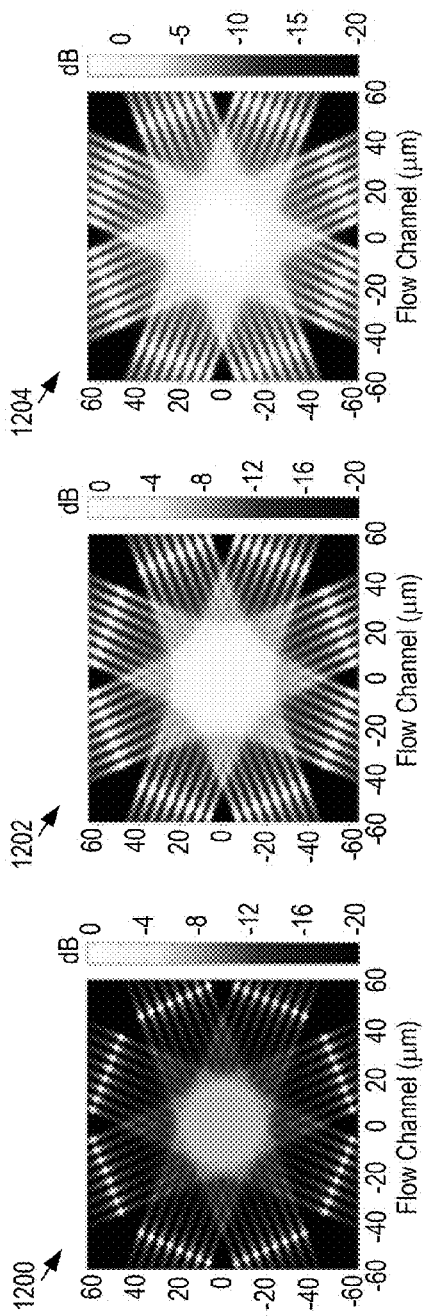
FIG. 12A
FIG. 12B
FIG. 12C
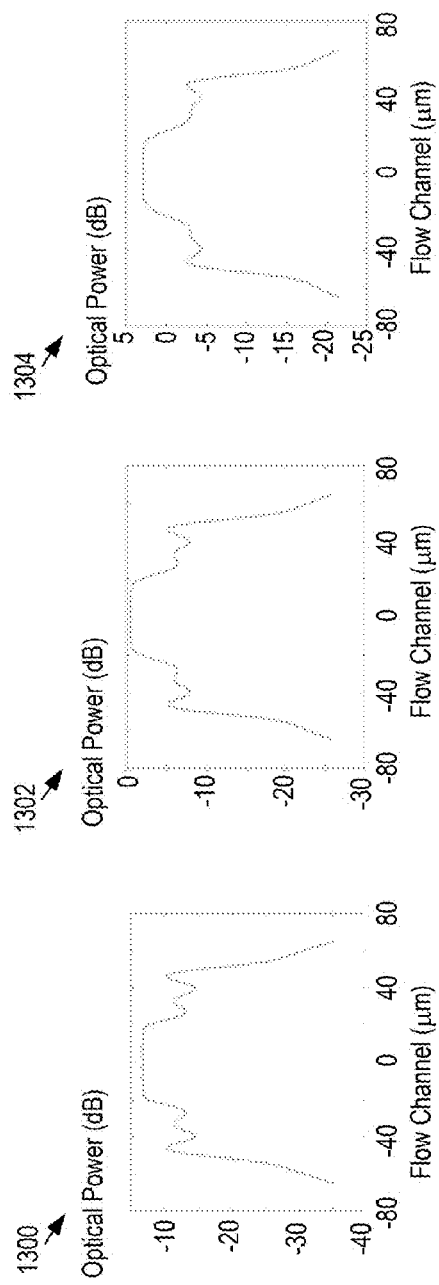
FIG. 13A
FIG. 13B
FIG. 13C

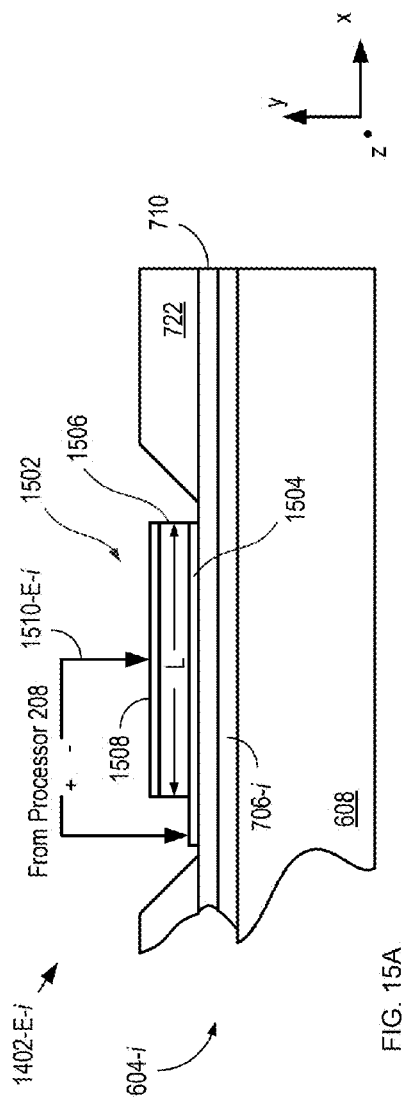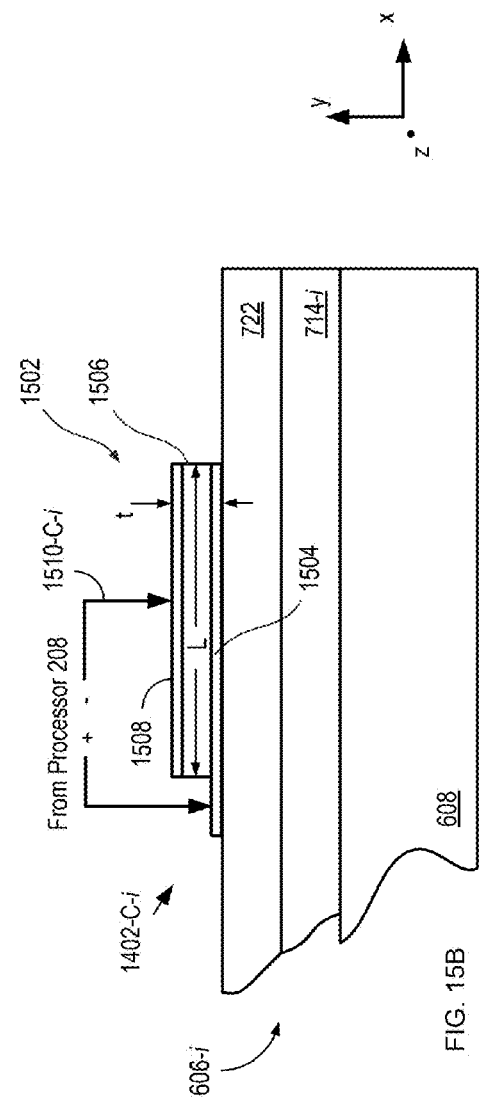

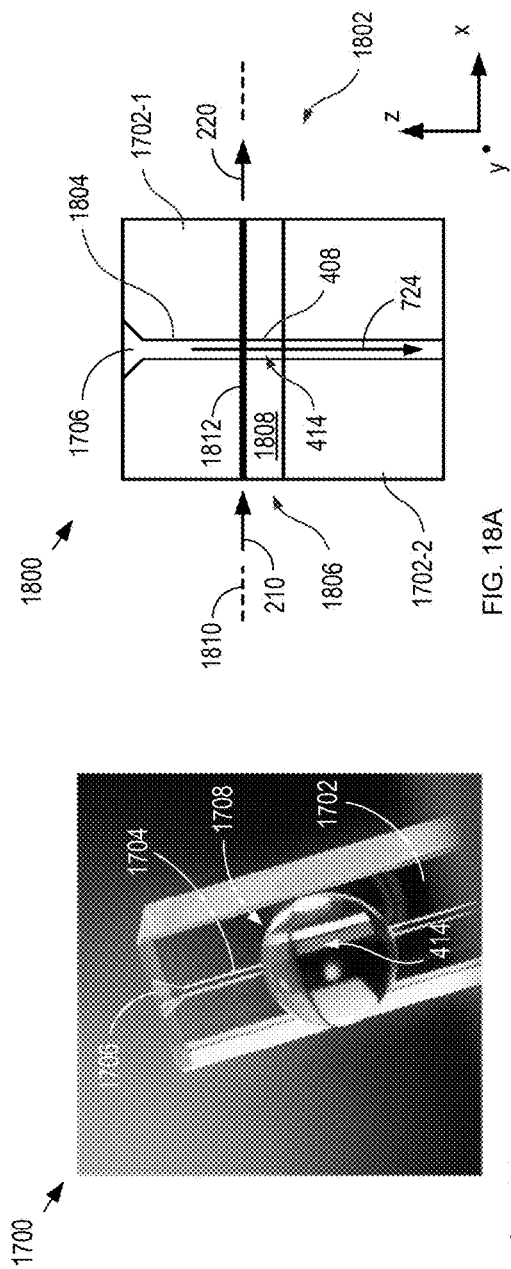
FIG. 17 (Prior Art)
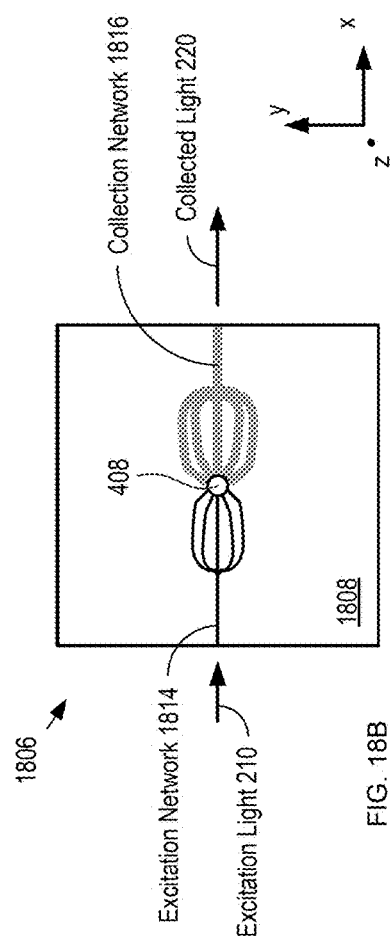
FIG. 18A
FIG. 18B

FLOW CYTOMETRY SYSTEM AND METHOD

CROSS-REFERENCE TO RELATED APPLICATIONS

This application is a continuation of co-pending U.S. patent application Ser. No. 14/321,138, filed Jul. 1, 2014, entitled "Flow Cytometry System and Method,", which is incorporated by reference.

FIELD OF THE INVENTION

The present invention relates to biotechnology in general, and, more particularly, to flow cytometry.

BACKGROUND OF THE INVENTION

Flow cytometry is a technique in which a fluid-flow system organizes cells within a stream of fluid such that the cells pass in single-file through a detection zone. As the cells pass through the detection zone, they are illuminated by laser light, which scatters from each cell in a manner that depends on its structure. Most modern flow cytometry approaches also employ numerous fluorochrome-labeled antibodies that selectively bind with specific cellular features, such as cell-associated molecules, proteins or ligands. When excited by light at their respective excitation wavelengths, each fluorochrome emits a characteristic fluorescence signal, indicating the presence of that fluorochrome-specific feature. The scattered light and fluorescence signals are detected and analyzed to classify and/or count the cells according to a set of parameters of interest. In some cases, once classified, the cells are sorted into sub-populations based on their particular characteristics.

Flow cytometry enables simultaneous multi-parameter analysis of individual cells in a fluid stream, such as analysis of cell surfaces and intracellular molecules, characterization and definition of different cell types in mixed cell populations, assessing the purity of isolated subpopulations, and analyzing cell size and volume. Flow cytometers are used in many clinical and biological applications, such as the diagnosis of blood cancers, basic research, clinical practice, and clinical trials.

Historically, fluid-flow systems in conventional flow cytometers have been of a stream-in-air configuration, in which the fluid stream is forced through a nozzle system so the cells pass in single file through a detection zone in open air. Other prior-art flow cytometers employ a flow cell configuration, wherein a sheath fluid hydrodynamically focuses the sample fluid into the core of an open stream that traverses the detection zone. Unfortunately, in each case, such prior-art flow cytometers have some significant disadvantages: (1) they are quite expensive; (2) they have a large footprint; (3) they are not easily portable; and (4) they require extensive time, expertise, and expense to use and maintain. In addition, systems having an open-flow design are difficult to adapt for use with infectious disease or pathogenic microbiological samples because of the risk of exposure.

To mitigate some of these disadvantages, microfluidics-based flow cytometers have been developed in which the sample fluid passes through the detection zone in an enclosed flow channel. The adoption of microfluidics approaches also enables increased on-chip functionality, such as filtering, cell sorting, and overall flow control.

Microfluidics-based flow cytometers are disclosed, for example, in U.S. Patent Publication No. 2009/0051912, which describes a flow cytometer system that is smaller and more portable than an open-flow system. In operation, the fluid-flow system is held under a microscope objective, which functions as an external optics system that provides the light used to interrogate the cells and collect light scattered or emitted from the detection zone.

In fact, most conventional flow cytometers rely on external optics for illuminating the detection zone and/or detecting the scattered light signals. Unfortunately, this limits how small and portable a flow cytometer can be made. In addition, careful alignment between the fluid-flow system and the external optics is critical for realizing precise and accurate measurements, and this alignment must be maintained during use to ensure proper system operation. Further exacerbating these issues, the use of several fluorochromes usually gives rise to a need for multiple lasers at different excitation wavelengths to excite the pallet of fluorochromes employed. Still further, numerous wavelength-filtered detectors are required to effectively discriminate between the resultant fluorescence signals. As a result, the use of external optics can add significant cost to a flow cytometry system.

Integrating optical surface waveguides with microfluidics fluid-flow systems offers some promise for mitigating some of the disadvantages of external optics-based flow cytometers. Examples of a microfluidics-based system having integrated optical surface waveguides are disclosed in U.S. Pat. No. 7,764,374, in which both fluid-flow channels and SU-8-based optical surface waveguides are formed on the top surface of a substrate. One SU-8 surface waveguide emits light into an analysis zone of the fluid-flow channel, while a second SU-8 surface waveguide, located across the fluid-flow channel, collects light after it has passed through the analysis zone.

In similar fashion, U.S. Patent Publication No. 2013/0083315 discloses flow cytometer arrangements having a first flow channel that includes a detection zone, and a plurality of "surface waveguide channels" that are adjacent to the detection zone. The surface waveguide channels are filled with fluid that laterally guides light captured from the detection zone to other regions of the substrate.

Unfortunately, such prior-art systems suffer from several disadvantages. It is often necessary to couple several independent light signals into or out of a single region. SU-8-based surface waveguides and fluid-filled surface waveguides require significant chip real estate, however. As a result, forming more than few optical surface waveguides that access the same location can be challenging.

Further, flow cytometry performance is improved when the detection zone is illuminated with substantially uniform light. Prior-art, microfluidics-based flow cytometers, however, are limited to providing illumination from one side of the fluid channel. As a result, uniform illumination of the sample fluid is precluded and system sensitivity is degraded.

SUMMARY OF THE INVENTION

The present invention enables lab-on-a-chip systems having improved illumination of a fluid stream and/or improved detection of light signals that arise from the fluid stream. As a result, embodiments of the present invention are able to provide better system performance, less measurement variation, and higher sensitivity than prior-art lab-on-a-chip systems. For example, lab-on-a-chip-based flow cytometers in accordance with the present invention can distinguish different subsets of cells with improved precision and can better quantify measurement parameters than flow cytometers known in the prior art. Although the present invention is particularly well suited for use in flow cytometers, it provides advantages in other lab-on-a-chip systems as well, such as spectrometers, and the like.

An illustrative embodiment of the present invention is a flow cytometry system having a fluid channel formed through the thickness of a substrate, and two sets of surface waveguides disposed on a surface of the substrate. Each set of surface waveguides is arranged such that its end facets form a circular arrangement around the flow channel. Each set of surface waveguides is formed in a different plane that is substantially orthogonal with the direction of fluid flow through the channel.

A first set of surface waveguides is used to illuminate the detection zone. Light from these excitation waveguides forms a substantially uniform illumination pattern in the flow channel. In some embodiments, the phase of the light in one or more of the excitation waveguides is controlled, thereby enabling control over the shape of the illumination pattern in the detection zone.

The second set of surface waveguides is used to capture light after it has interacted with the fluid in the detection zone. In some embodiments, the phase of the light in one or more of these collection waveguides is controllable. In some embodiments, at least one of the collection waveguides is optically coupled with a wavelength filter that discriminates spectral information in the light coupled into that collection waveguide.

In some embodiments, at least one set of surface waveguides is arranged such that their facets form a polygonal arrangement around the flow channel. In some of these embodiments, each side of the polygon includes a plurality of surface waveguide facets.

An embodiment of the present invention is an apparatus comprising: a substrate that defines a first plane, the substrate comprising a flow channel that is operative for conveying fluid along a first direction that is substantially orthogonal to the first plane, the flow channel being located within a first region of the substrate; a first surface waveguide that is optically coupled with the flow channel, the first surface waveguide being located in a second plane within the first region, wherein the second plane is substantially parallel with the first plane; and a second surface waveguide that is optically coupled with the flow channel in the first region, the second surface waveguide being located in a third plane within the first region, wherein the third plane is substantially parallel with the second plane.

Another embodiment of the present invention is an apparatus comprising: a substrate having a thickness between a first major surface and a second major surface; a first flow channel that is operative for conveying fluid through the thickness; a first plurality of surface waveguides, each of the first plurality of surface waveguides being optically coupled with the flow channel in a first region, the first plurality of surface waveguides being coplanar in a first plane within the first region; and a second plurality of surface waveguides, each of the second plurality of surface waveguides being optically coupled with the flow channel, the second plurality of surface waveguides being coplanar in a second plane within the first region; wherein, the first major surface, the second major surface, the first plane, and the second plane are substantially parallel.

Yet another embodiment of the present invention is a method comprising: conveying a first fluid along a first direction through a first region; interrogating the first fluid with a first illumination pattern that is based on a first light signal emitted from a first surface waveguide that lies in a first plane that is orthogonal to the first direction in the first region; and coupling a first portion of the first illumination pattern into a second surface waveguide that lies in a second plane that is orthogonal to the first direction in the first region, wherein the first portion is coupled into the second surface waveguide after the first illumination pattern has interacted with the first fluid.

BRIEF DESCRIPTION OF THE DRAWINGS

FIGS. 12A-C depict simulated illumination patterns across detection zone 1106 for different wavelengths of light.

FIGS. 13A-C depict plots of random phase field distribution across detection zone 1106 for different wavelengths of excitation light.

FIGS. 15A and 15B depict cross-section views of phase-control elements 1402-E-i and 1402-C-i, respectively, in accordance with the second alternative embodiment of the present invention.

FIG. 17 depicts a picture of a conventional flow cytometer flow cell in accordance with the prior art.

FIGS. 18A-B depict a flow cytometry flow cell in accordance with a third alternative embodiment of the present invention.

DETAILED DESCRIPTION

Figure 1A:
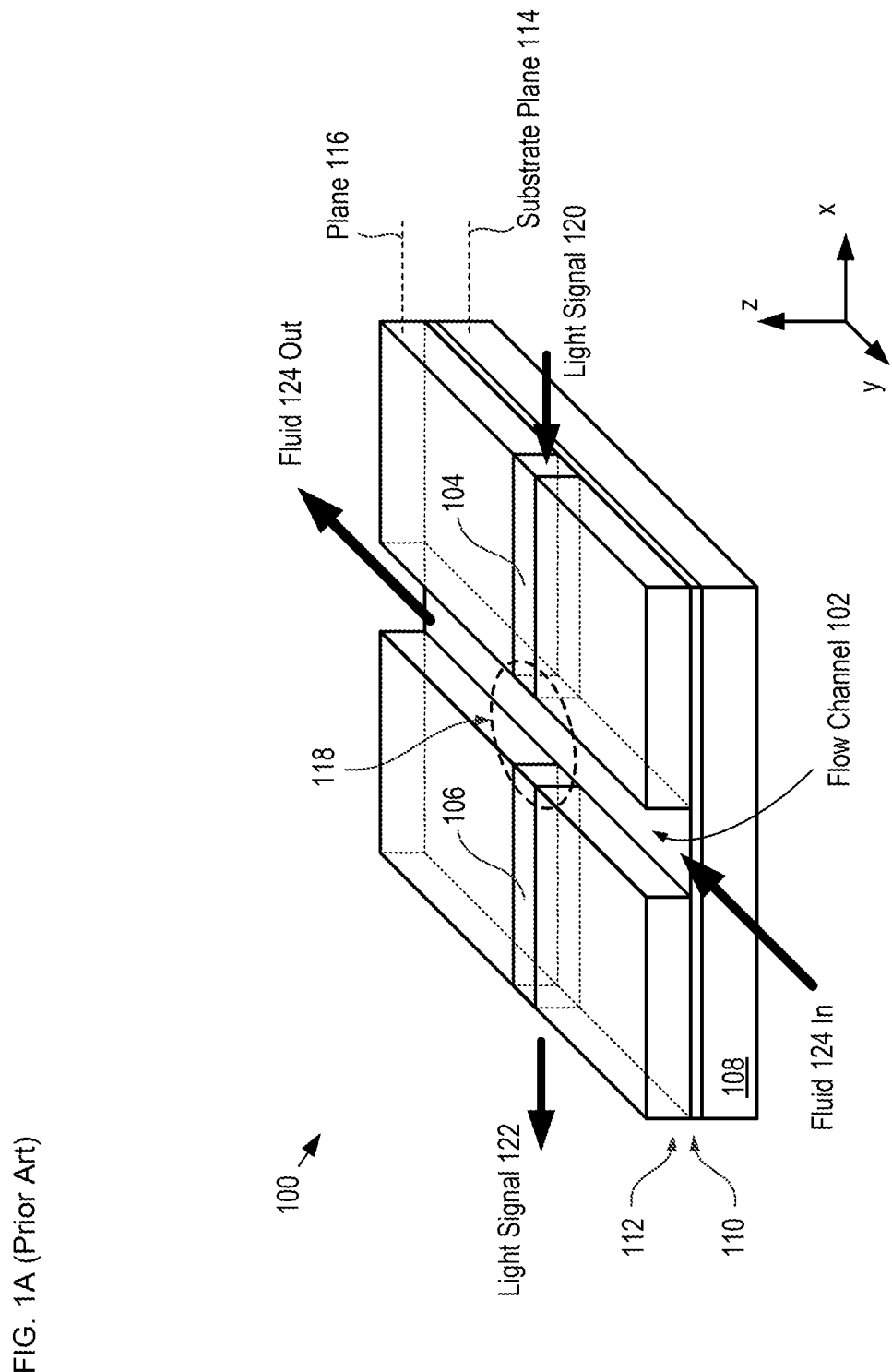
FIGS. 1A-C depict examples of prior-art microfluidic systems with integrated surface waveguides.
Figure 1B:
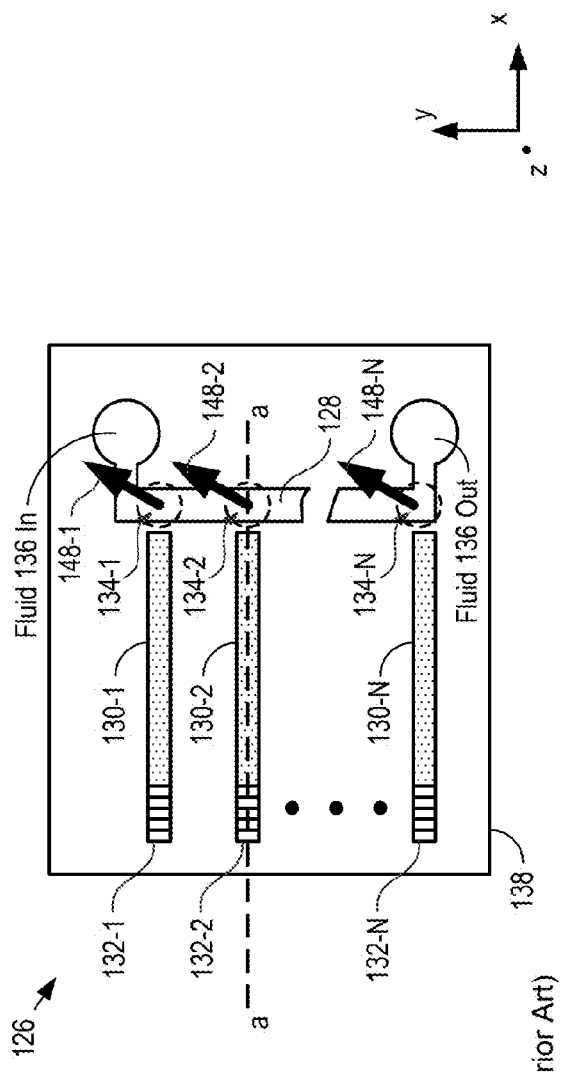
Figure 1C:
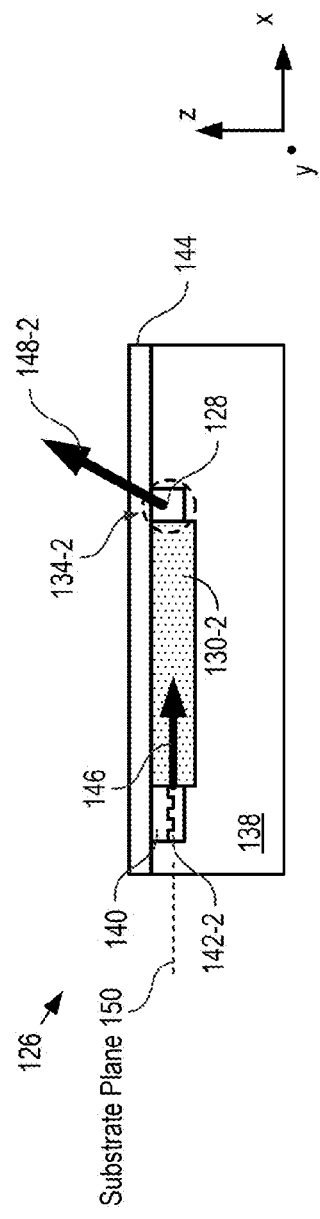

FIGS. 1A-C depict examples of prior-art microfluidic systems with integrated surface waveguides.

FIG. 1A depicts a portion of a Micro Total Analysis System (μTAS) that includes flow channel 102, illumination waveguide 104, and collection waveguide 106, all of which are formed on the top surface of substrate 108. System 100 is in accordance with lab-on-a-chip (LOC) systems disclosed by J. Hubner, et al., in U.S. Pat. No. 7,764,374, issued Jul. 27, 2010, which is incorporated herein by reference.

System 100 is an example of an absorption spectroscopy system. In operation, illumination waveguide 104 emits light signal 120 into analysis zone 118, which is defined by the area between illumination waveguide 104 and collection waveguide 106. Fluid 124 absorbs certain characteristic wavelengths of the light based on the constituents of the fluid. Some of the light not absorbed by the fluid is captured as light signal 122 by collection waveguide 106, which carries the light to a wavelength dispersion system (not shown) that enables its spectral analysis.

Illumination waveguide 104 and collection waveguide 106, as well as flow channel 102, are formed on the top surface of substrate 108. Substrate 108 typically comprises silicon, on which a layer of silicon dioxide (i.e., lower cladding 110) is formed as a lower cladding layer for the waveguides. Substrate 108 defines substrate plane 114, which is aligned with the x-y plane.

Each of the waveguides comprises a core region of SU-8 that is surrounded by layer 112, which acts to laterally confine light signals 120 and 122 in the waveguides. Layer 112 is typically a layer of silicon dioxide disposed on lower cladding layer 110. It should be noted that layer 112 defines plane 116, which is parallel to substrate plane 114. Flow channel 102 and waveguides 104 and 106 are all coplanar in plane 116.

To complete the waveguide structures and enclose flow channel 102, a second substrate (not shown for clarity) having a third layer of silicon dioxide is bonded to layer 112.

While mitigating some of the drawbacks related to microfluidics-based analytical systems discussed above, system 100 still has some significant drawbacks. For example, by forming all surface waveguides and flow channels such that they are coplanar, optical access to analysis zone 118 is limited to primarily only one surface waveguide pair. As a result, simultaneous interrogation of analysis zone by more than one light signal travelling along diverse paths is precluded. In order to interrogate fluid 110 with multiple light signals, therefore, multiple pairs of illumination and collection waveguides are required, which leads to increased chip real estate for system 100 and commensurately higher cost. Further, in applications where it is desirable to collect light scattered by material in analysis zone 118, only forward-scattered light can be collected via a collection waveguide. Surface waveguides formed at positions to capture side-scattered light would, in general, be separated by a relatively large distance, making it difficult for a surface waveguide to capture sufficient light for a reliable measurement. Further, the use of SU-8 in system 100 can lead to degradation over time, particularly when the system is used for short wavelengths and/or high intensities, due to absorption of the light.

FIGS. 1B-C depicts schematic drawings of a top and cross-section view, respectively, of another example of a lab-on-a-chip system having integrated microfluidics and surface waveguides. System 126 is an example of a portion of a partially integrated flow cytometer. System 126 includes flow channel 128, surface waveguides 130-1 through 130-N, and lasers 132-1 through 132-N. System 126 is in accordance with flow cytometers described by C. Vannahme, et al., in "Plastic lab-on-a-chip for fluorescence excitation with integrated organic semiconductor lasers," Optics Express, Vol. 19, No. 9, pp. 8179-8186 (2011), which is incorporated herein by reference.

System 126 includes flow channel 128, surface waveguides 130 and laser 132, all of which are monolithically integrated on substrate 138. Like system 100 described above, all flow channels and surface waveguides are coplanar in substrate plane 150.

Substrate 138 is a poly(methyl methacrylate) (PMMA) substrate into which flow channel 128 and depressions 140 are formed using conventional plastic imprinting techniques. Depressions 140 are formed such that the bottom of each depression is characterized by a nascent grating structure 142, which is later coated with a thin film of organic semiconductor tris(8-hydroxyquinoline) aluminum ($Alq_3$) to form organic semiconductor lasers 132.

Surface waveguides 130 are formed directly in the PMMA material by exposing it to deep UV light, which breaks the molecular chains in the PMMA material to locally increase its refractive index. The unexposed PMMA retains its original, lower refractive index enabling it to serve as cladding material for the waveguides.

After the surface waveguides have been defined, PMMA cover 144 is joined to substrate 138 to complete the fabrication of system 126.

In operation, lasers 132 are optically pumped to generate light signals 146-1 through 146-N, which couple into surface waveguides 130-1 through 130-N, respectively. Light signals 146 are used to excite the different fluorochromes used to stain analytes in fluid 136. As the cells in the fluid flow sequentially through each of detection zones 134-1 through 134-N, fluorochromes selectively bound to features of the cells fluoresce at their characteristic fluorescence wavelengths as light signals 148-1 through 148-N.

Fluorescence signals 148 propagate out of plane 150 and are detected via a free-space optics-based detection system.

The need to provide different detection zones so that multiple excitation signals can be used to excite the full pallet of fluorochromes adds significant complexity to system 126 and its operation. For example, because the fluorochromes are not excited simultaneously, ambiguity can creep into the measurement results. Further, the need for an external free-space detection system mitigates many of the benefits of integrating flow channel 128 and surface waveguides 130. Still further, as discussed above, multiple detection zones requires more chip real estate, which leads to higher system cost.

The present invention enables improved flow cytometry by arranging a plurality of surface waveguides in a plane that is not co-planar with the direction in which a flow channel conveys a fluid. As a result, the facets of the surface waveguides can be arranged on different sides of the flow channel. The present invention, therefore, enables greater control over the manner in which the fluid is illuminated. It also improves the ability to collect light from the flow channel by enabling collection of light close to the flow channel even though the light exits the flow channel along different directions.

It should be noted that, while the present invention is particularly well suited for flow cytometry, it can also provide similar advantages in other microfluidic applications, such as spectroscopy, chemical synthesis, capillary electrophoresis, lab-on-a chip applications, and the like.

Figure 2:
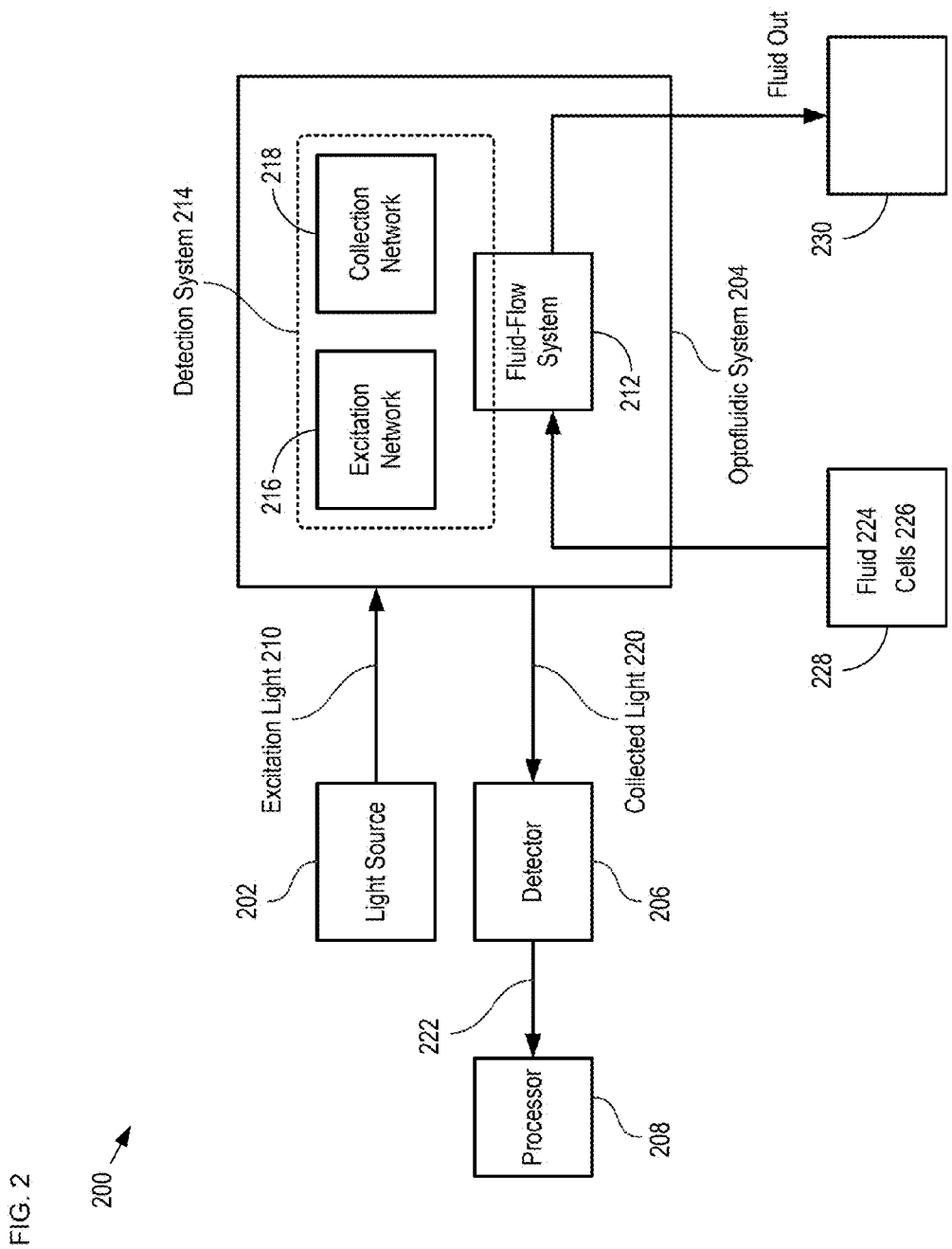
FIG. 2 depicts a block diagram of a flow cytometer in accordance with an illustrative embodiment of the present invention.

FIG. 2 depicts a block diagram of a flow cytometer in accordance with an illustrative embodiment of the present invention. Flow cytometer 200 includes light source 202, optofluidic system 204, detector 206, and processor 208.

System 200 is operative for analyzing cells 226, which are contained in liquid-phase fluid 224. In some embodiments, system 200 is operative for other particles contained in a liquid-phase medium. In some embodiments, system 200 is operative for particles and/or cells contained in a gas-phase medium (e.g., air, etc.). In some applications, system 200 is operative for a gas-phase or liquid-phase fluids that are substantially particle-free.

Figure 3:
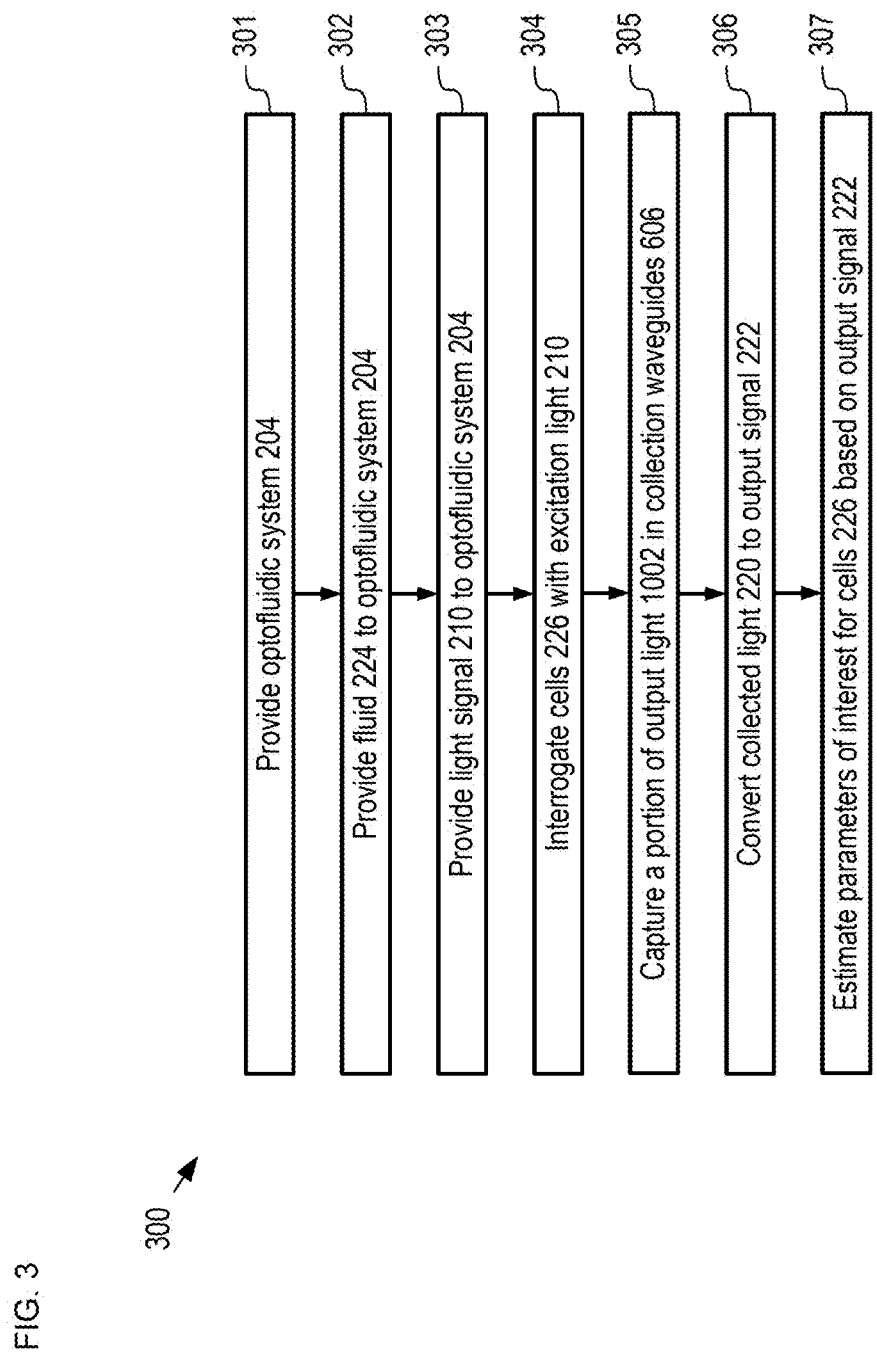
FIG. 3 depicts operations of a method for performing flow cytometry in accordance with the illustrative embodiment.

FIG. 3 depicts operations of a method for performing flow cytometry in accordance with the illustrative embodiment. Method 300 begins with operation 301, wherein optofluidic system 204 is provided. Method 300 is described herein with continuing reference to FIG. 2, as well as reference to FIGS. 4-10.

Optofluidic system 204 is a monolithically integrated system that includes fluid-flow system 212 and detection system 214. Detection system 214 comprises surface-waveguide-based excitation network 216, surface-waveguide-based collection network 218, and a portion of fluid-flow system 212. Optofluidic system 204 is described in more detail below and with respect to FIGS. 4-9.

Figure 4:
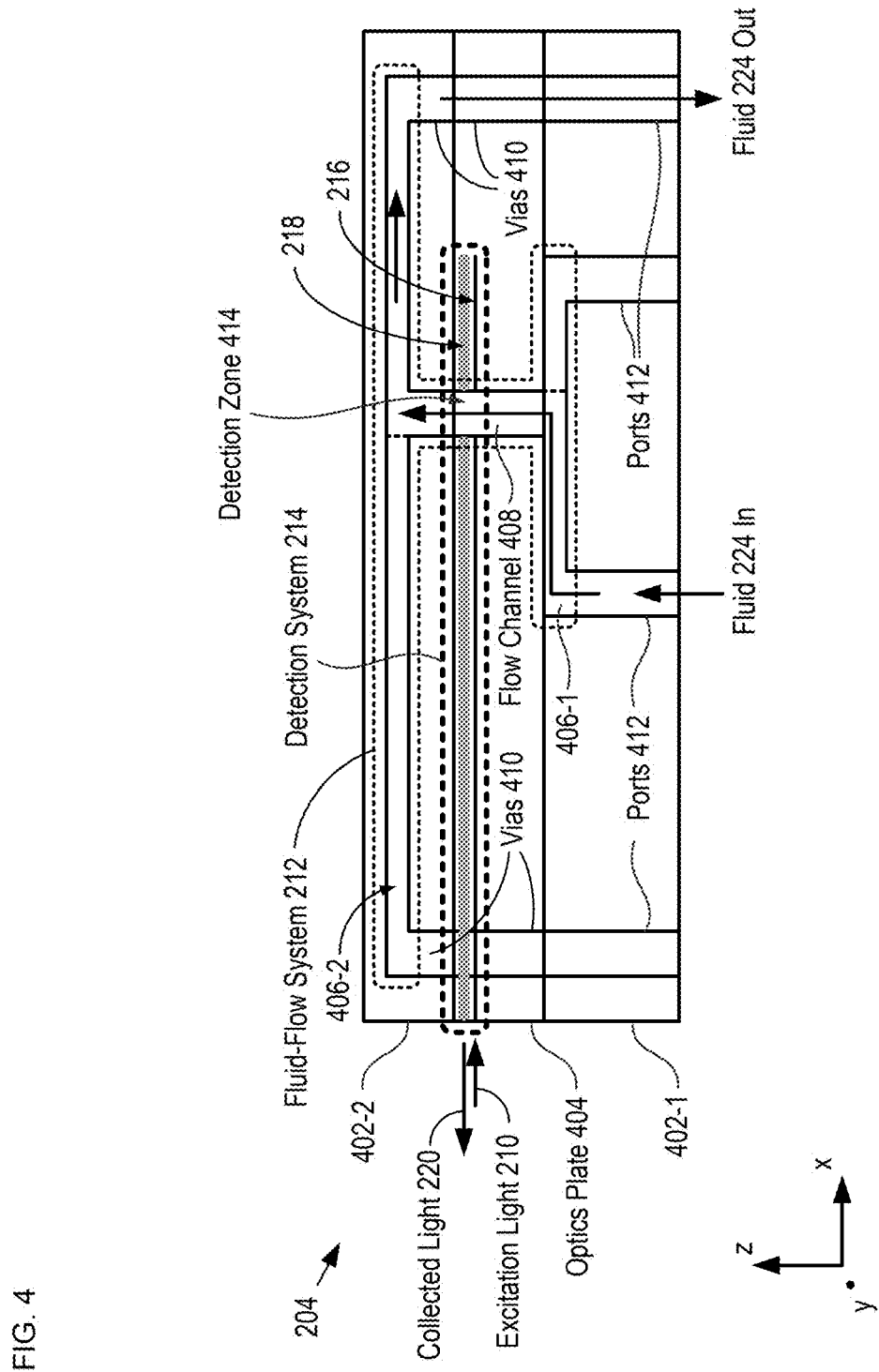
FIG. 4 depicts a schematic drawing of a cross-sectional view of an optofluidic system in accordance with the illustrative embodiment of the present invention.

FIG. 4 depicts a schematic drawing of a cross-sectional view of an optofluidic system in accordance with the illustrative embodiment of the present invention. Optofluidic system 204 includes channel plates 402-1 and 402-2, and optics plate 404. These plates collectively define each of fluid-flow system 212 and detection system 214.

Figure 5:
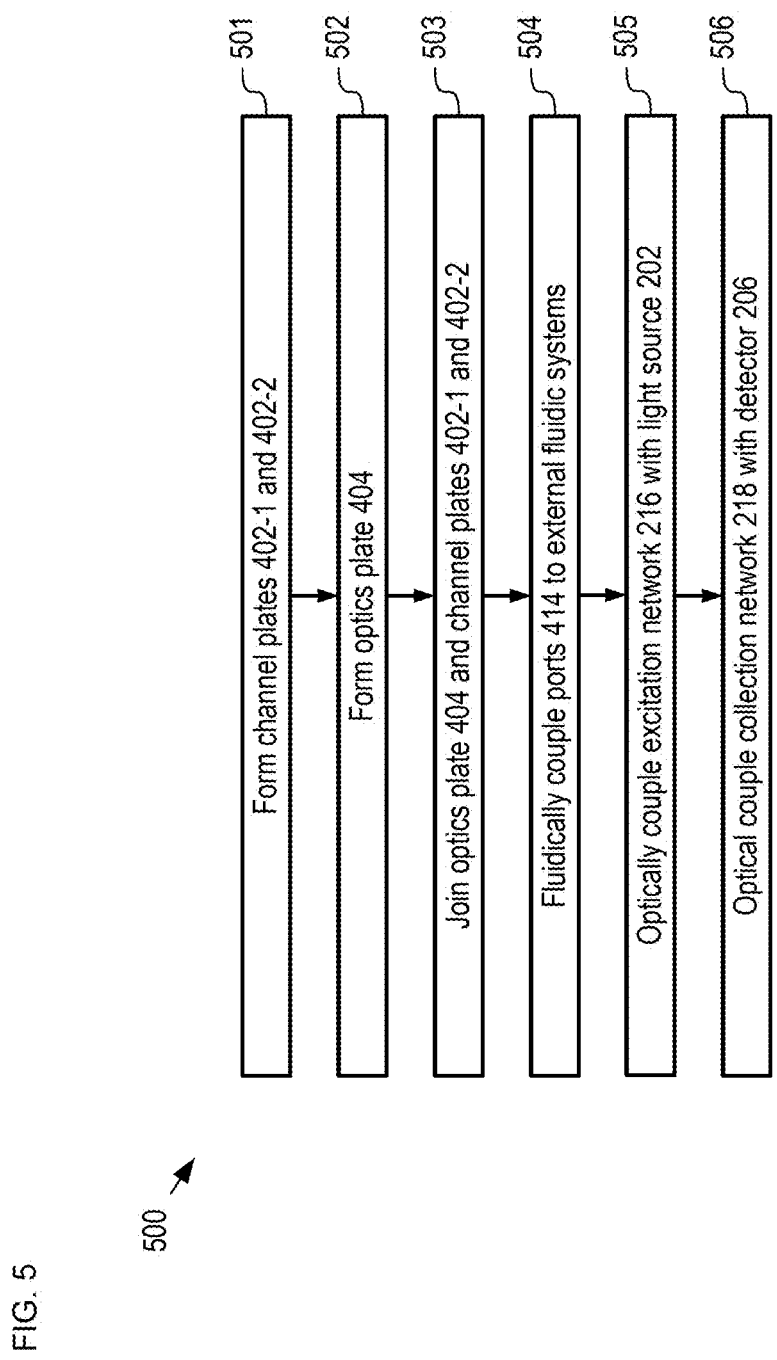
FIG. 5 depicts operations of a method for forming optofluidic system 204.

FIG. 5 depicts operations of a method for forming optofluidic system 204. Method 500 begins with operation 501, wherein channel plates 402-1 and 402-2 are formed.

Each of channel plates 402-1 and 402-2 is a conventional microfluidic channel plate formed via conventional methods (e.g., reactive-ion etching (RIE), wet-chemical etching, sand-blasting, etc.). Channel plates 402-1 and 402-2 include channel networks 406-1 and 406-2, respectively, each of which is formed in a conventional planar processing substrate. Channel plates 402-1 and 402-2 also include vias 410 and ports 412 distributed among the channel plates and optics plate 404 to enable interconnection of the channel networks to each other and interconnection of fluid-flow system 212 to external facilities, such as fluid sources, waste containers, etc.

Typically, for optical systems such as the illustrative embodiment, the channel plate substrates are made of fused silica because it does not exhibit significant autofluorescence. In some applications, however, the channel plate substrates comprise a material other than fused silica. Materials suitable for use in the channel plate substrates include, without limitation, glasses (e.g., silicon dioxide, borofloat glass, quartz, Pyrex, etc.), semiconductors (e.g., silicon, silicon carbide, germanium, GaAs, InP, etc.), metals, ceramics, plastics, composite materials, and the like.

Each of channel networks 406-1 and 406-2 is a system of microfluidic channels suitable for, in combination with flow channel 408, performing conventional fluidic operations on fluid 224, such as flow separation, filtering, mixing, sorting, etc., as well as forcing the cells in fluid 224 to flow in single-file order through flow channel 408. The specific arrangement and functionality of channel networks 406-1 and 406-2 is typically a matter of application-based design. Channel networks 406-1 and 406-2, flow channel 408, vias 410, and ports 412 collectively define fluid-flow system 212.

At operation 502, optics plate 404 is formed.

Figure 6:
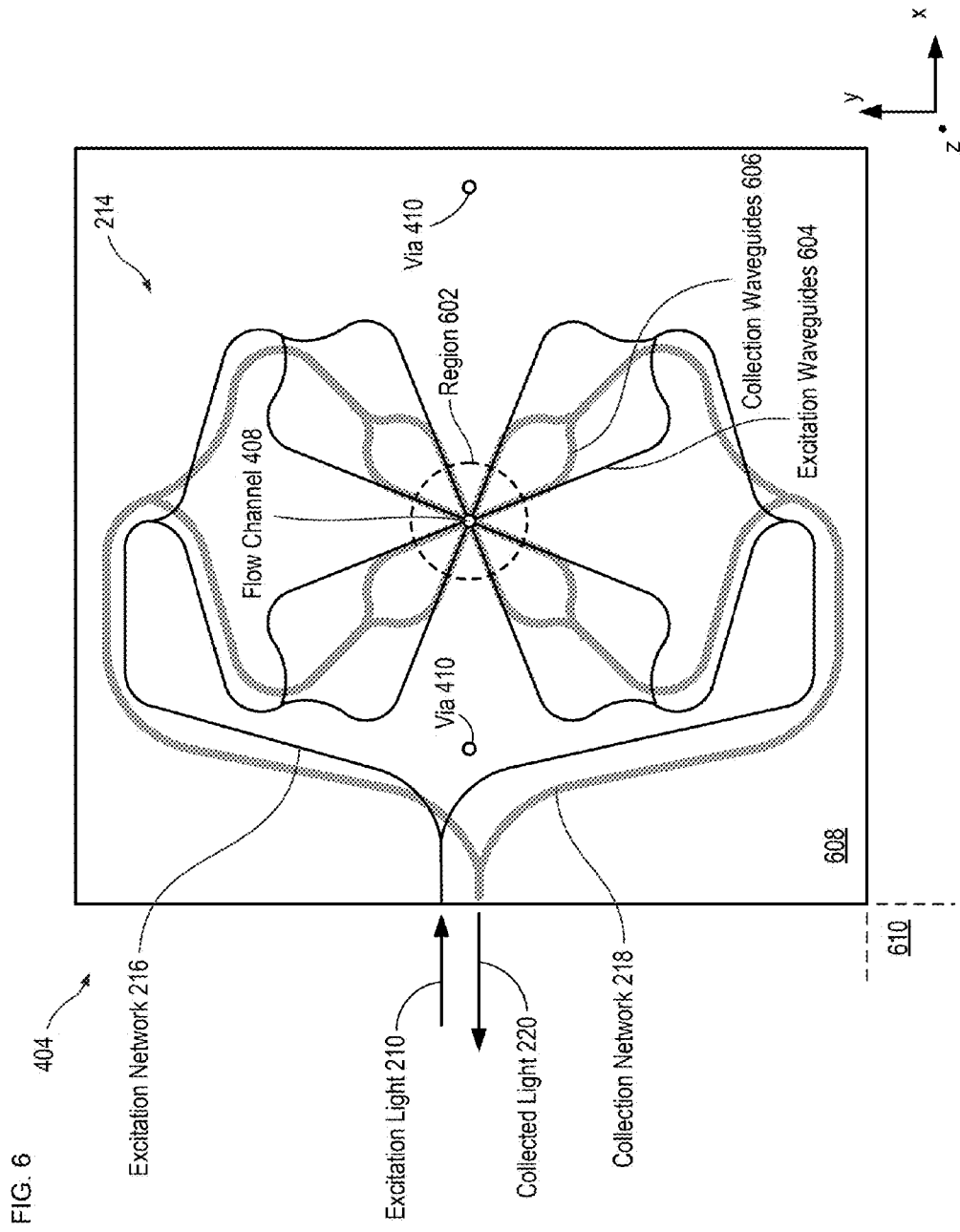
FIG. 6 depicts a top view of optics plate 404.

FIG. 6 depicts a top view of optics plate 404. Optics plate 404 includes flow channel 408, excitation network 216, collection network 218, flow channel 408, and vias 410. In some embodiments, optics plate 404 is an element provided as a portion of a conventional flow-cytometer flow chamber to, for example, improve or replace a conventional optical excitation or collection system.

Each of excitation network 216 and collection network 218 includes a plurality of N surface waveguides (referred to, individually, as excitation waveguide 604-$i$ or collection waveguide 606-$i$, where $1 \leq i \leq N$). Although N=8 in the illustrative embodiment, it will be clear to one skilled in the art, after reading this Specification, how to specify, make, and use alternative embodiments of the present invention wherein N is equal to any practical number, and can be as small as one. Further, one skilled in the art will recognize that excitation network 216 and collection network 218 can include different numbers of surface waveguides.

In the illustrative embodiment, collection waveguides 606 are disposed in a plane located above excitation waveguides 604 in region 602. In some embodiments, collection waveguides 606 are not disposed above excitation waveguides. Further, in some embodiments, excitation waveguides 604 lie in a plane that is above the plane of collection waveguides 606. Still further, in some embodiments, at least some of excitation waveguides 604 and collection waveguides 606 lie in the same plane. In other embodiments, at least one of the pluralities of excitation waveguides 604 and collection waveguides 606 is distributed among two or more waveguide layers.

Figure 7A:
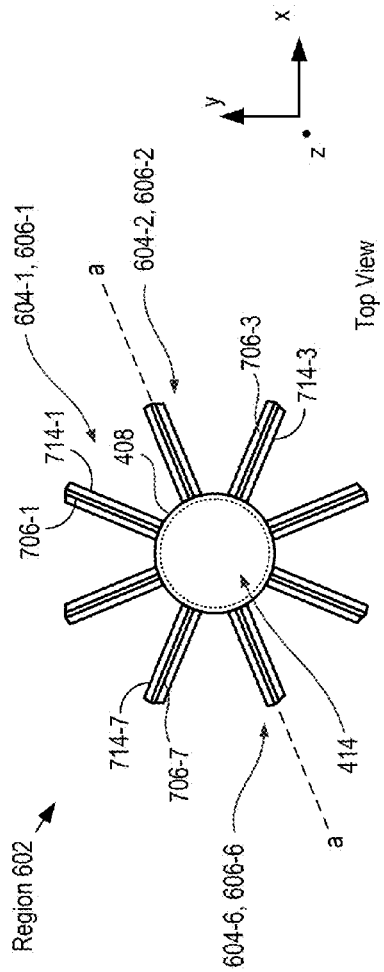
FIGS. 7A-B depict top and cross-sectional views of region 602 of optics plate 404.
Figure 7B:
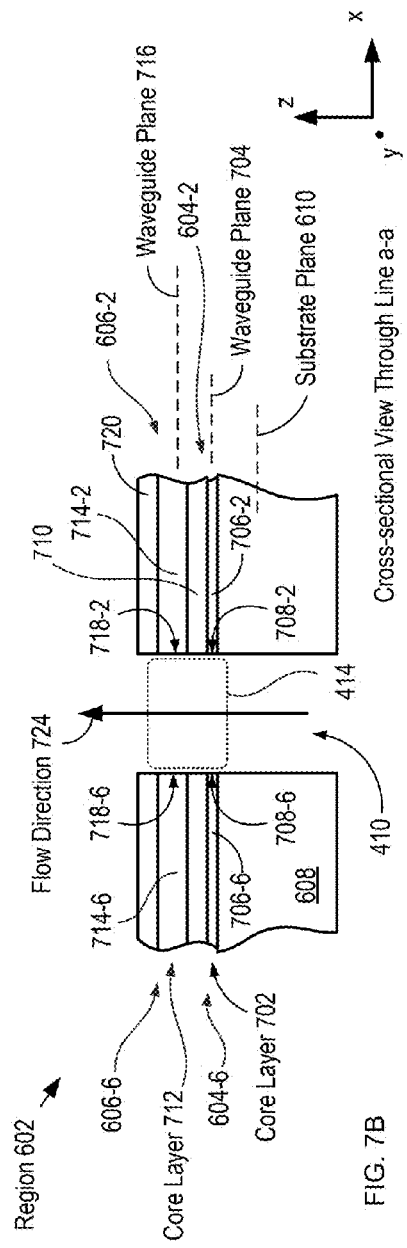

FIGS. 7A-B depict top and cross-sectional views of region 602 of optics plate 404. Region 602 provides a detailed view of flow channel 408, excitation waveguides 604-1 through 604-8, and collection waveguides 606-1 through 606-8. Within region 602, excitation waveguides 604 and collection waveguides 606 are formed on substrate 608 such that their end facets are arranged in a substantially circular arrangement about the center of flow channel 408. One skilled in the art will recognize, after reading this Specification, that the region of flow channel 408 that is surrounded by the end facets of excitation waveguides 604 and collection waveguides 606 substantially defines detection zone 414.

Figure 8:
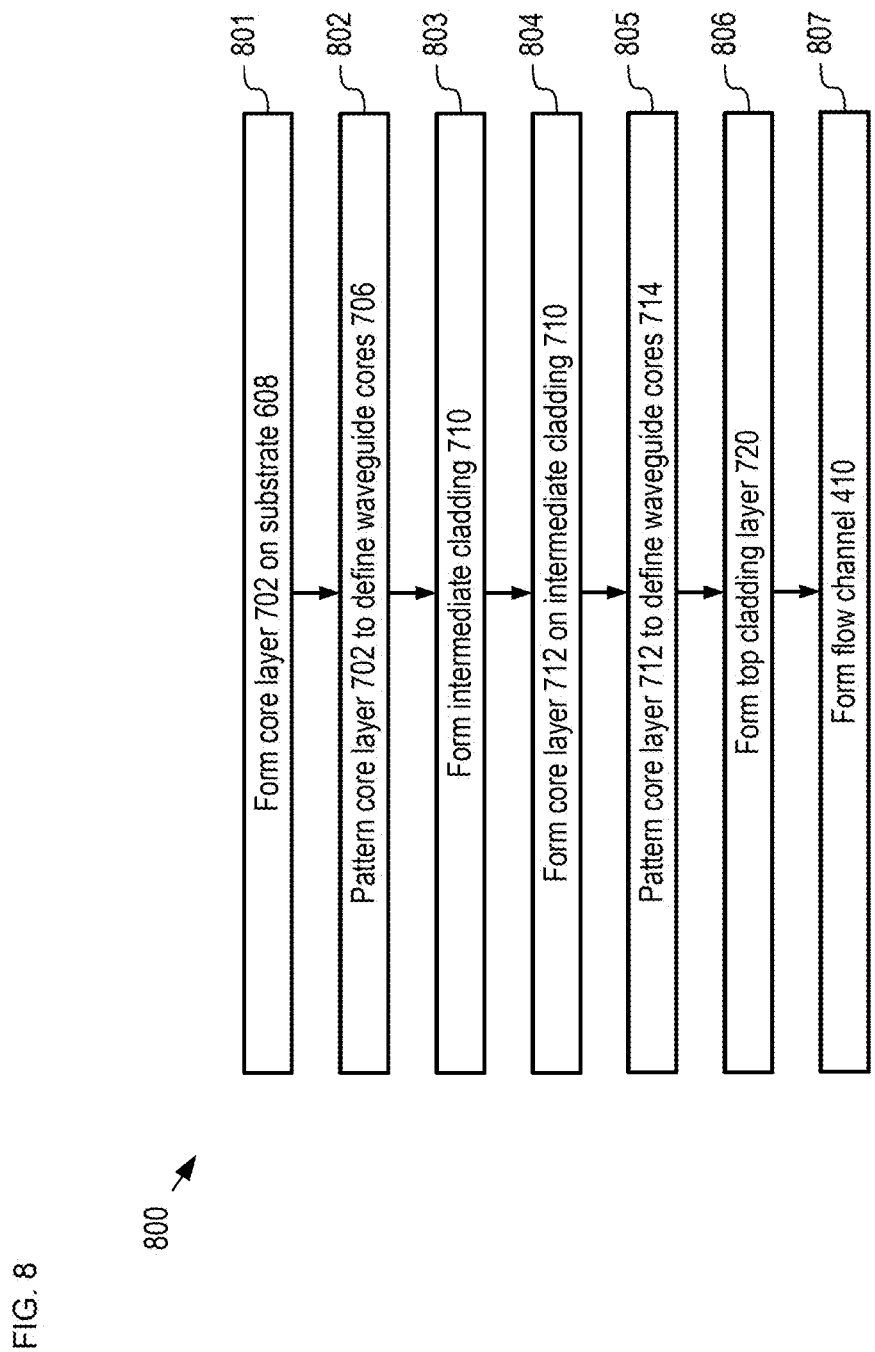
FIG. 8 depicts sub-operations suitable for use in forming optics plate 404.

FIG. 8 depicts sub-operations suitable for use in forming optics plate 404. Operation 502 begins with sub-operation 801, wherein core layer 702 is formed on the top surface of substrate 608.

Substrate 608 is a planar substrate that is analogous to the channel plate substrates described above and, in the illustrative embodiment, comprises fused silica in order to suppress autofluorescence. In some embodiments, however, substrate 608 can comprise another material, as discussed above and with respect to channel plates 402-1 and 402-2. Substrate 608 defines substrate plane 610, which lies generally in the x-y plane, as indicated.

Core layer 702 is a conventional planar layer of stoichiometric silicon nitride, deposited on the top surface of substrate 608 using low-pressure chemical vapor deposition (LPCVD). Core layer 702 has a thickness of approximately 25 nanometers (nm) and defines waveguide plane 704. In some embodiments, core layer 702 has a different thickness. In some embodiments, core layer 702 comprises a material other than silicon nitride. Materials suitable for use in core layer 702 include any material through which excitation signals can propagate. In some embodiments, core layer 702 is formed with a different suitable formation process.

In some embodiments, substrate 608 includes a surface layer, such as a silicon oxide, that functions as a lower cladding layer for waveguides formed from core layer 702.

At operation 802, core layer 702 is patterned in conventional fashion to define waveguide cores 706-1 through 706-8 (referred to, collectively, as waveguide cores 706). Typically, core layer 702 is patterned via photolithography and RIE. Waveguide cores 706 are patterned such that each has a width within the range of approximately 1 micron to approximately 4 microns, and typically approximately 2 microns As a result, each of waveguide cores 706 defines a stripe waveguide that is suitable for single-mode operation at the wavelengths of light included in excitation light 210. Each of waveguide cores 706 includes an end facet 708, the plurality of which is arranged in a substantially circular arrangement about detection zone 414.

In some embodiments, at least one of waveguide cores 706 comprises different materials, is of a different waveguide type, and/or has different dimensions (i.e., thickness or width) than another of surface waveguide cores 706. Different core materials, types, and/or dimensions enable surface waveguides that are preferable for, for example, different wavelengths, diverse functions (e.g., providing light to or collecting light from detection zone 414, etc.), and the like. In some embodiments, therefore, at least one of operation 801 and 802 is repeated one or more times.

Figure 9A:
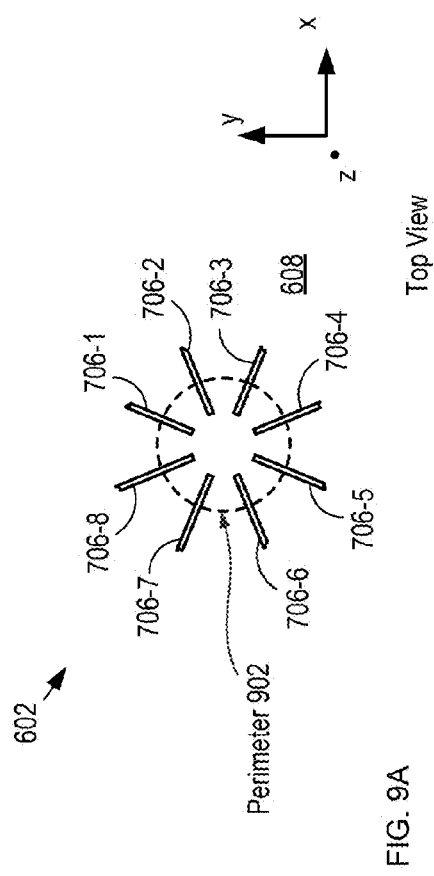
FIG. 9A depicts a schematic drawing of a top view of region 602 after the definition of waveguide cores 706.

FIG. 9A depicts a schematic drawing of a top view of region 602 after the definition of waveguide cores 706.

At operation 803, intermediate cladding 710 is formed in conventional fashion. Intermediate cladding 710 is a layer of silicon dioxide deposited via LPCVD. Typically, after formation, intermediate cladding 710 is planarized via chemical-mechanical polishing, or another suitable planarization technique. Intermediate cladding 710 has a thickness that is typically within the range of approximately 1 microns to approximately 30 microns. Intermediate cladding 710 operates as both an upper cladding for excitation waveguides 604 and a lower cladding for detection waveguides 606.

One skilled in the art will recognize that the thickness of intermediate cladding 710 is a matter of design and is based on several factors, such as the acceptable level of cross-talk between excitation network 216 and collection network 218, acceptable levels of loss in the excitation and collection waveguides, and the like.

In some embodiments, intermediate cladding 710 is formed via another deposition technique, such as plasma-enhanced chemical vapor deposition (PECVD), sputtering, spin-on glass deposition, and the like. In some embodiments, intermediate cladding 710 comprises a material other than silicon dioxide. One skilled in the art will recognize that the choice of material for intermediate cladding 710 is based on numerous factors, including the wavelength of light, the materials of substrate 608 and core layers 702 and 712, material compatibility with fluid 224, etc.

At operation 804, core layer 712 is formed on intermediate cladding 710. Core layer 712 is analogous to core layer 702 described above; however, core layer 712 is formed such that it has a thickness of approximately 100 nm. Core layer 712 defines waveguide plane 716.

At operation 805, core layer 712 is patterned in conventional fashion to define stripe waveguide cores 714-1 through 714-8 (referred to, collectively, as waveguide cores 714), which collectively define waveguide plane 716. Waveguide plane 716 is substantially parallel with substrate plane 610. Typically, core layer 712 is patterned via photolithography and RIE.

In order to facilitate collection of light from detection zone 414, waveguide cores 714 are patterned such that they have width within the range of approximately 1 micron to approximately 4 microns, and typically approximately 2 microns. As a result, each of waveguide cores 714 operates as a multimode waveguide core for the wavelengths of light in collected light 220. Like waveguide cores 706, waveguide cores 714 have end facets 718, which are arranged in a substantially circular arrangement about detection zone 414. In some embodiments, waveguide cores 714 have a different width or height.

The dimensions for waveguide cores 706 (and/or waveguide cores 714 provided herein are merely exemplary. One skilled in the art will recognize that the specific dimensions of a waveguide depend on system and application considerations, and that any suitable dimensions for these waveguides is within the scope of the present invention.

Further, as discussed above vis-à-vis waveguide cores 706, in some embodiments, at least one of waveguide cores 714 comprises different materials, is of a different waveguide type, and/or has different dimensions (i.e., thickness or width) than another of surface waveguide cores 714. Different core materials, types, and/or dimensions enable surface waveguides that are preferable for, for example, different wavelengths, diverse functions (e.g., providing light to or collecting light from detection zone 414, etc.), and the like. In some embodiments, therefore, at least one of operation 804 and 805 is repeated one or more times.

Figure 9B:
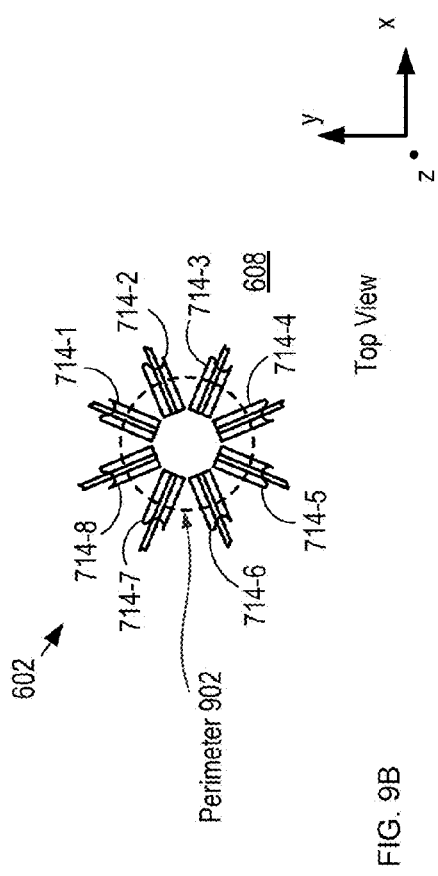
FIG. 9B depicts a schematic drawing of a top view of region 602 after the definition of waveguide cores 714.

FIG. 9B depicts a schematic drawing of a top view of region 602 after the definition of waveguide cores 714.

At operation 806, top cladding layer 720 is formed on waveguide cores 714 to complete formation of collection waveguides 606. Top cladding layer 720 is analogous to intermediate cladding layer 710.

It should be noted that, at the end of operation 806, each of waveguide cores 706 and 714 extends past perimeter 902, which defines the extent flow channel 408 as it will be formed in operation 807. This ensures that each of the pluralities of end facets 708 and 718 will be arranged in a circular pattern located at the edge of the flow channel once it is formed, since the end facets are formed by the deep-RIE process used to form the flow channel. In some embodiments, the end facet of at least one surface waveguide is not formed during the operation in which flow channel 408 is formed. In some embodiments, one or more of end facets 708 and 718 is formed when its respective core layer is patterned to define its corresponding waveguide cores.

Although the illustrative embodiment comprises excitation waveguides that operate as single-mode waveguides and collection waveguides that operate as multimode waveguides, it will be clear to one skilled in the art, after reading this Specification, how to specify, make, and use alternative embodiments of the present invention comprising at least one excitation waveguide that operates as a multimode waveguide and/or at least one collection waveguide that operates as a single-mode waveguide.

In some embodiments, collection waveguides 606 are routed individually to the edge of substrate 608 and detected independently. Such an arrangement can, for example, enable maintenance of angle-dependent scattering information.

At operation 807, flow channel 408 is formed through the thickness of substrate 608 and its surface layers. Flow channel 408 has a diameter within the range of approximately 20 microns to approximately 120 microns, and is typically approximately 40 microns, which restricts cells in fluid 224 to single-file flow through detection zone 414. It should be noted that the present invention is applicable to applications other than flow cytometry, wherein the size of flow channel 408 does not necessarily restrict the size of particles or cells in fluid 224. One skilled in the art will recognize, therefore, that the diameter of flow channel 408 is a matter of application-based design considerations.

Although in the illustrative embodiment, flow channel 408 is formed via conventional deep-RIE, it will be clear to one skilled in the art, after reading this Specification, how to specify, make, and use alternative embodiments wherein flow channel 408 is formed via a different process, such as sand blasting, laser ablation, wet etching, etc., are also suitable for the formation of the flow channel depending on the materials used in system 200.

Returning now to method 500, at operation 503, channel plates 402-1 and 402-2 are joined with optics plate 404 such that channel networks 406-1 and 406-2 are fluidically coupled with flow channel 408. In the illustrative embodiment, the plates are joined using a wafer bonding technique, such as fusion bonding, thermo-anodic bonding, etc., to fuse the three plates into a single monolithic element. In some embodiments, the plates are joined via another suitable method, such as clamping, etc. In some embodiments, a fluidic seal is formed between the fluidic elements on each plate using intervening elements, such as O-rings, gaskets, deposited material (e.g., polyimide, SU-8, PMMA, etc.) and the like.

At operation 504, ports 414 are fluidically coupled with external fluidic systems, such as a reservoir, pumping system, and waste container for fluid 224.

At operation 505, excitation network is optically coupled with light source 202.

Light source 202 is a conventional multi-spectral light source that provides excitation light having wavelengths suitable for exciting the full pallet of fluorochromes used during operation of flow cytometer 200. In some embodiments, light source 202 includes a plurality of light emitting devices and/or spectral filters, such as lasers, light-emitting diodes (LEDs), superluminescent diodes, and the like.

At operation 506, collection network is optically coupled with detector 206.

Detector 206 is a conventional detection system operative for detecting one or more of the wavelengths included in collected light 220, which is received from optofluidic system 204. Detector 206 includes a plurality of detectors and wavelength filters suitable for discriminating fluorescence signals and scattered signals collected by collection network 216. Detector 206 provides output signal 222 to processor 208.

Processor 208 is a conventional processing system operative for receiving output signal 222 and conducting analysis of the output signal to estimate one or more parameters of fluid 224 and/or cells 226.

Returning now to method 300, at operation 302, fluid 224 is pumped through optofluidic system 212, from reservoir 228 to waste container 230, such that its constituent cells 226 flow through detection zone 414 along flow direction 724. Flow direction 724 is aligned with the z-direction, as depicted in FIG. 7B, which is orthogonal to each of substrate plane 610, and waveguide planes 704 and 716. In some embodiments, flow direction 724 is not orthogonal with waveguide planes 704 and 716; however, it should be noted that it is an aspect of the present invention that flow direction 724 is neither parallel nor coplanar with either of the waveguide planes.

At operation 303, light source 202 provides light signal 210 to optofluidic system 204.

At operation 304, cells 226 are interrogated with excitation light 210.

Figure 10:
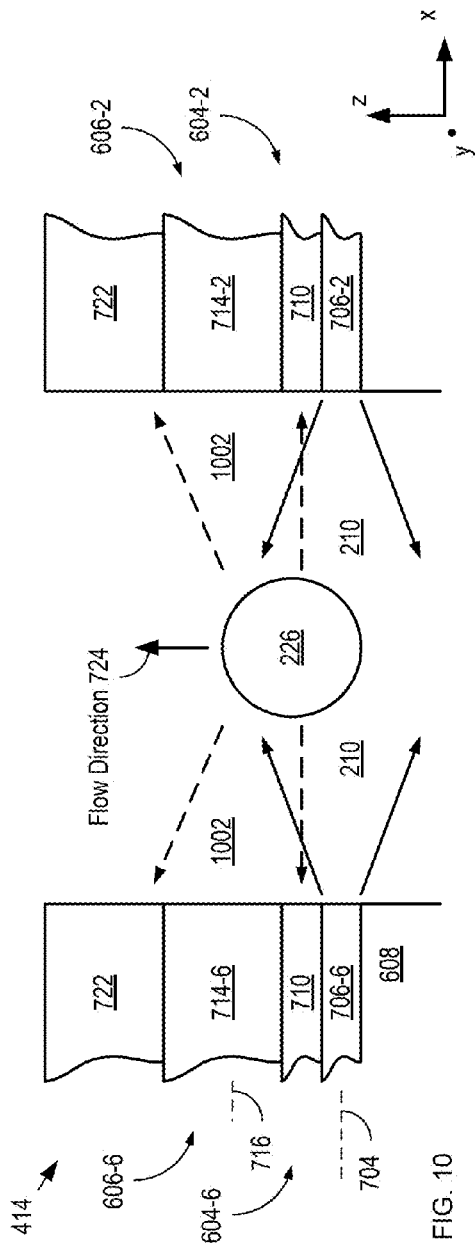
FIG. 10 depict a side view of detection zone 414 during interrogation of a cell 226.

FIG. 10 depicts a side view of detection zone 414 during interrogation of a cell 226. Excitation light is provided to cell 226 by excitation waveguides 604.

Interrogation of cell 226 with excitation light 210 gives rise to output light 1002, which includes forward-scattered, side-scattered, and fluorescent light signals as discussed above.

At operation 305, collection waveguides 606 capture a portion of output light 1002 as collected light 220.

At operation 306, collection waveguides 606 convey collected light 220 to detector 206, which converts it into output signal 222.

At operation 307, processor 208 performs analysis of output signal 222 and provides an estimate of the parameters of interest for cells 226.

Figure 11:
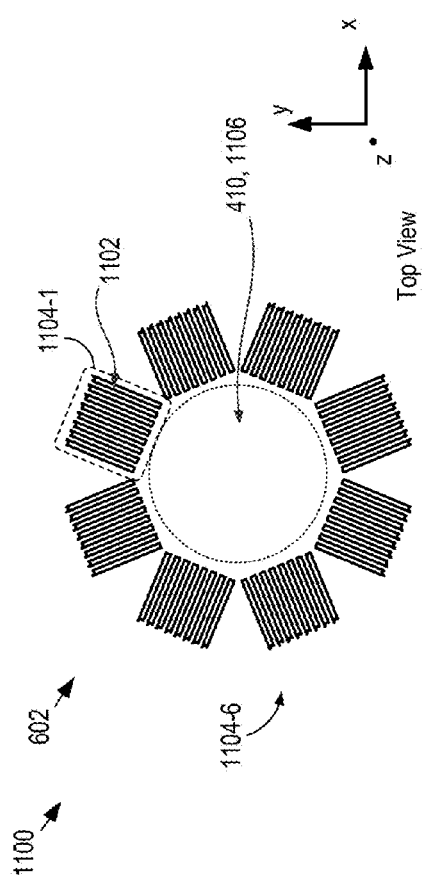
FIG. 11 depicts a schematic drawing of a top view of region 602 in accordance with a first alternative embodiment of the present invention.

FIG. 11 depicts a schematic drawing of a top view of region 602 in accordance with a first alternative embodiment of the present invention. System 1100 is analogous to system 200 described above; however, system 1100 includes excitation and collection waveguide pairs that are arranged in arrays that collectively form a polygonal arrangement that surrounds flow channel 408.

Each waveguide pair 1102 includes one excitation waveguide 604 and one collection waveguide 606, as described above and with respect to FIGS. 7A-B.

Waveguide pairs 1102 are arranged in waveguide arrays 1104-1 through 1104-8 (referred to, collectively, as waveguide arrays 1104), each of which includes eight waveguide pairs arranged in linear fashion. Waveguide arrays 1104 form an octagonal arrangement that is concentric with flow channel 408. Although in the example shown, waveguide arrays 1104 form a polygon having eight sides, it will be clear to one skilled in the art, after reading this Specification, how to specify, make, and use alternative embodiments wherein waveguide arrays 1104 form a polygon having any practical number of sides. Further one skilled in the art will recognize that waveguide arrays 1104 can include any practical number of waveguide pairs.

The arrangement of waveguide arrays 1104 about flow channel 408 gives rise to detection zone 1106 having a substantially circular cross-section. In some embodiments, detection zone 1106 has a cross-sectional shape other than circular.

FIGS. 12A-C depict simulated illumination patterns across a diameter of a detection zone for different wavelengths of excitation light.

Patterns 1200, 1202, and 1204 show the illumination pattern across a 120-micron diameter flow channel for TM-polarized light at wavelengths of 404, 532, and 632 nm, respectively.

FIGS. 13A-C depict plots of random phase field distribution across detection zone 1106 for different wavelengths of excitation light.

Plots 1300, 1302, and 1304 depict the distribution of optical power across a 160-micron diameter flow channel for TE-polarized light at wavelengths of 404, 532, and 632 nm, respectively.

FIGS. 12 and 13 evince that substantially uniform illumination can be realized by providing excitation light from an octagonal pattern of waveguide arrays in accordance with the first illustrative embodiment.

Although the waveguide arrangements described above enable significant improvement in illumination of a flow channel region, the illumination pattern for any wavelength is determined purely by the arrangement of the facets about the region and are not controllable during operation. It would be desirable to enable control over the shape of the illumination pattern during use, however.

It is another aspect of the present invention that control over the illumination pattern in the detection zone can be gained by controlling the phase and/or amplitude of the light launched by one or more excitation waveguides into detection zone 414. In some embodiments, this enables beam shaping capable of providing specific illumination patterns having local intensity maxima at discrete positions within detection zone 414.

Further, identification of the light signals captured by an individual collection waveguide can also be improved by controlling the phase of the light signal in that waveguide.

In some embodiments, at least one of collection waveguides 606 is a single-mode waveguide that includes a polarization filter. Further, in some of these embodiments, excitation light 210 is provided is polarized (e.g., as TM light). In such a configuration, the present invention enables detection of light that is partially converted to another polarization mode (e.g., TE), which provides an indication as to particle shape (e.g., ratio of diameter versus length, etc.), as described by N. G. Khlebtsov, et al., in "Can the Light Scattering Depolarization Ratio of Small Particles Be Greater Than 1/3?" *J. Phys. Chem. B*
, Vol. 2005, No. 109, pp. 13578-13584 (2005), which is incorporated herein by reference.

Figure 14:
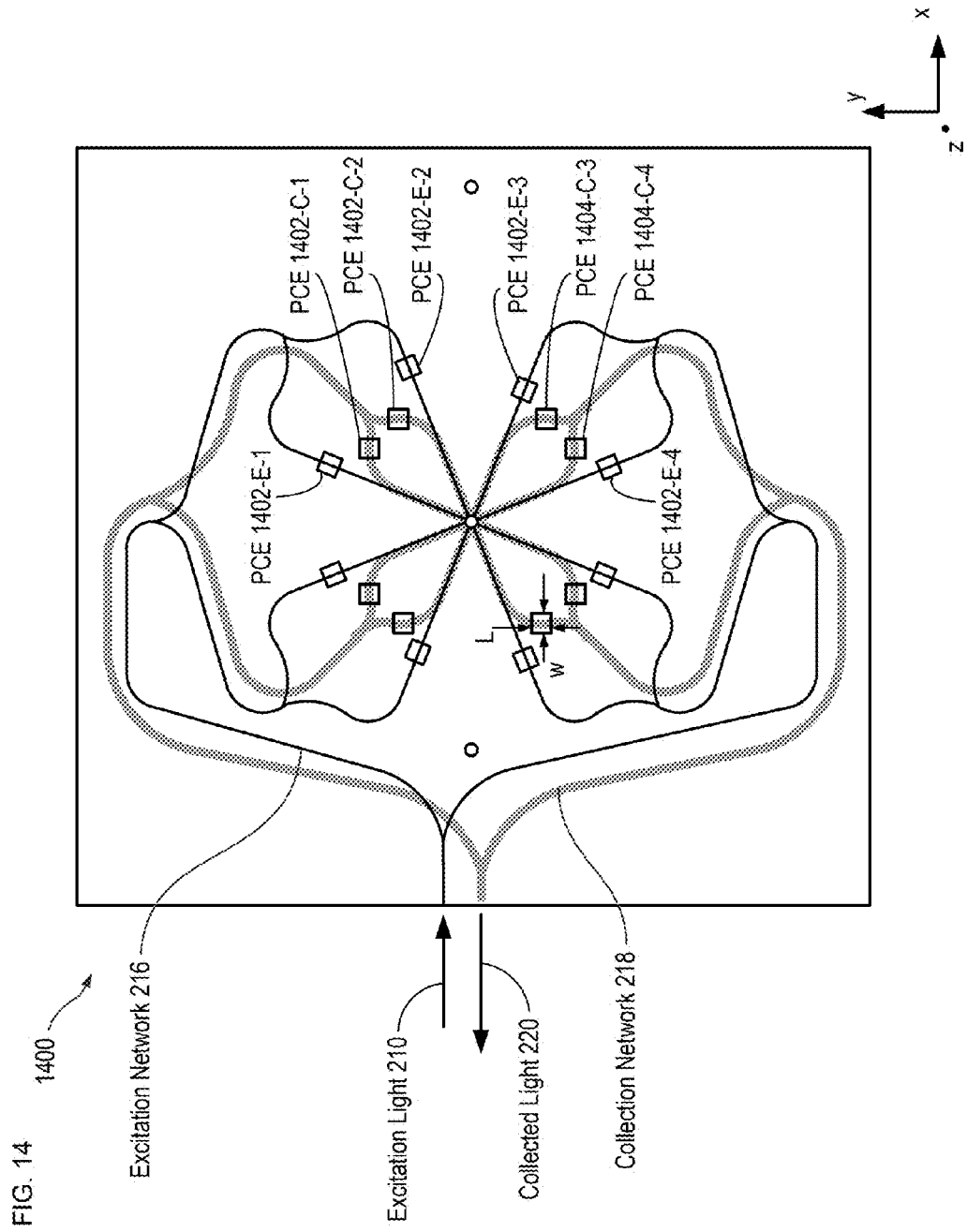
FIG. 14 depicts an optics plate in accordance with a second alternative embodiment of the present invention.

FIG. 14 depicts an optics plate in accordance with a second alternative embodiment of the present invention. Optics plate 1400 is analogous to optics plate 404 and includes all of the same structure; however, optics plate 1400 also includes phase-control elements 1402-E-1 through 1402-E-8 and phase-control elements 1402-C-1 through 1402-C-8 (referred to, collectively, as PCE 1402-E and PCE 1402-C, respectively). Each of phase-control elements 1402-E and 1402-C is operatively coupled with an excitation waveguide or collection waveguide such that it can control the phase of a light signal propagating through the waveguide.

FIGS. 15A and 15B depict cross-section views of phase-control elements 1402-E-i and 1402-C-i, respectively, in accordance with the second alternative embodiment of the present invention. Each of phase-control elements 1402-E-i and 1402-C-i comprises strain element 1502 that is operatively coupled with its respective waveguide core. Strain element 1502 includes lower electrode 1504, piezoelectric layer 1506, and upper electrode 1508.

Each of lower electrode 1504 and upper electrode 1508 is a layer of electrically conductive material, such as platinum, gold, aluminum, etc. The thickness of lower electrode 1504 and upper electrode 1508 is a matter of design choice.

Piezoelectric layer 1506 is a layer of piezoelectric material, such as lead zirconate titanate (PZT), having thickness, t. Piezoelectric layer 1506 is patterned to form a substantially rectangular region on which upper electrode 1508 is formed. One skilled in the art will recognize that the width, w, and length, L, of upper electrode 1508 (where w is the dimension of the layer along the direction transverse to the axial direction of its underlying waveguide and L is the dimension of the layer along the axial direction of its underlying waveguide) effectively define the operative dimensions of strain element 1502. As discussed below and with respect to FIG. 16, the operational characteristics of PCE 1402-E and PCE 1402-C are based on the values of t, w, and L.

In some embodiments, one or both of piezoelectric layer 1506 and lower electrode 1504 are not patterned and, therefore, remain over the entire surface of the substrate. In such embodiments, vias are formed through the piezoelectric material to enable electrical contact to be established to the underlying lower electrode.

In PCE 1402-E-i, strain element 1502 is disposed on intermediate cladding 710 in a region where core layer 712 has been removed during patterning of collection waveguide cores 714.

In PCE 1402-C-i, strain element 1502 is disposed upper cladding 722 in a region where core layer 702 has been removed during patterning of excitation waveguide cores 706.

Processor 208 provides control signals 1510-E-i and 1510-C-i to each of PCE 1402-E-i and PCE 1402-C-i, respectively. These control signals apply a voltage differential between lower electrode 1504 and upper electrode 1508, which gives rise to strain in piezoelectric layer 1506. This strain is transmitted into the underlying waveguide core, resulting in a change in its effective refractive index.

In similar fashion, the phase of light propagating through collection waveguide 606-i is controlled by control signal 1508-C-i, provided by processor 208. Control signal 1508-C-i is a voltage differential applied to lower electrode 1504 and upper electrode 1508, disposed on upper cladding 722, as shown. Application of a voltage differential to the electrodes of PCE 1402-C-i give rise to strain in piezoelectric layer 1506, which is transmitted into waveguide guide core 714-i, resulting in a change in its refractive index.

Figure 16:
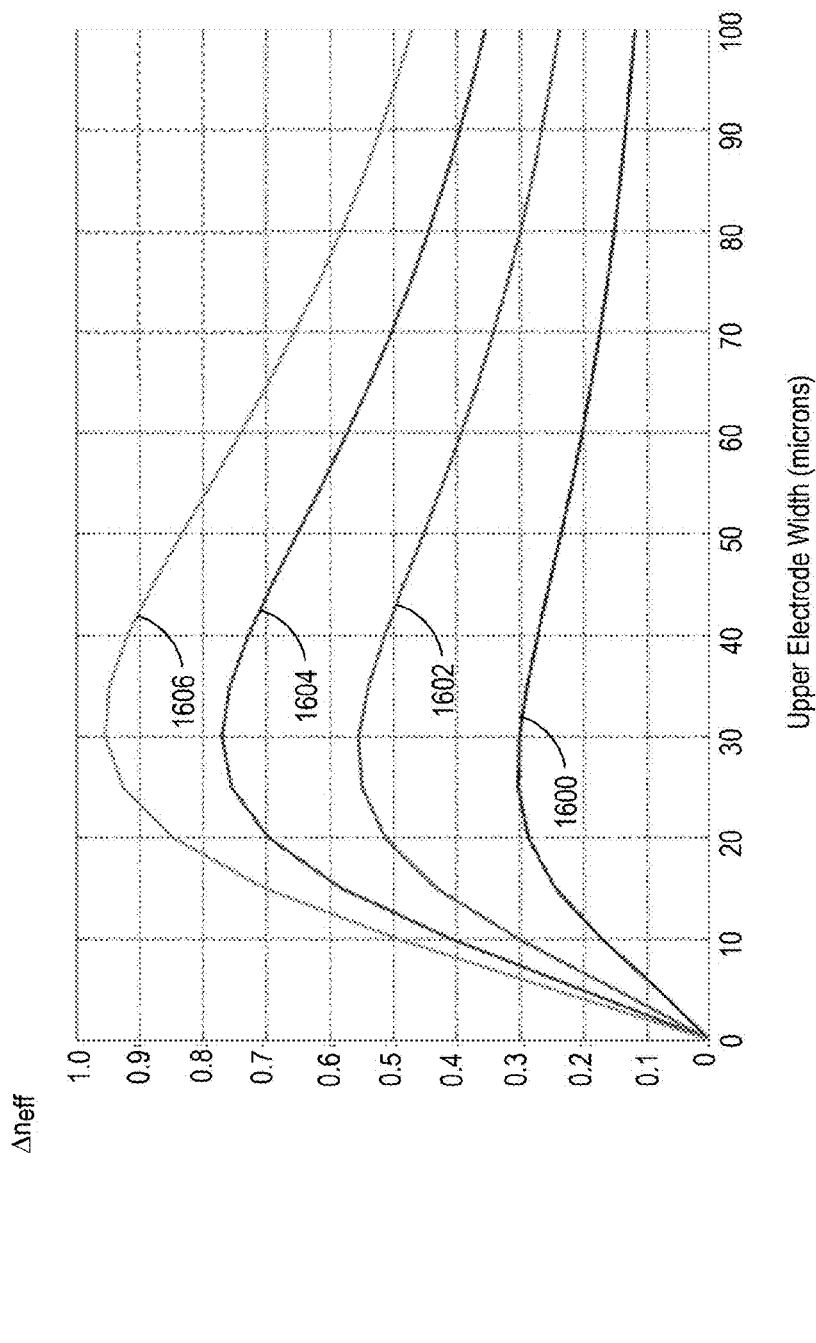
FIG. 16 depicts simulation results for the change in effective refractive index for excitation waveguide core 706-as a function of thickness, length, and width of piezo-electric layer 1506.

FIG. 16 depicts simulation results for the change in effective refractive index for excitation waveguide core 706-i as a function of the thickness of piezoelectric layer 1506 and the length, L, and width, w, of upper electrode 1508.

Plot 1600 shows the change in refractive index for excitation waveguide core 706-i, as a function of upper electrode width, w, for a piezoelectric layer 1506 having a thickness of 0.5 micron and a upper electrode length of 13.99 mm.

Plot 1602 shows the change in refractive index for excitation waveguide core 706-i, as a function of upper electrode width, w, for a piezoelectric layer 1506 having a thickness of 1.0 micron and a upper electrode length of 7.66 mm.

Plot 1604 shows the change in refractive index for excitation waveguide core 706-i, as a function of upper electrode width, w, for a piezoelectric layer 1506 having a thickness of 1.5 micron and a upper electrode length of 5.51 mm.

Plot 1606 shows the change in refractive index for excitation waveguide core 706-i, as a function of upper electrode width, w, for a piezoelectric layer 1506 having a thickness of 2.0 micron and a upper electrode length of 4.45 mm.

Plots 1600 through 1606 that a significant change in refractive index can be achieved in a waveguide core operatively coupled with strain element 1502, which will give rise to a commensurate change in phase for a light signal propagating through the waveguide.

One skilled in the art will recognize that piezoelectric-layer-based PCE 1042 is merely one example of a phase control element within the scope of the present invention. For example, phase can be controlled via thermo-optic modulation (i.e., via a heater disposed on a waveguide), birefringence modulation using a magnetostrictive element, etc. Further, in some embodiments, control over the illumination pattern in the detection zone is provided by controlling amplitude of the light launched by one or more excitation waveguides using an amplitude modulator, such as a Mach-Zehnder interferometer structure.

In some embodiments, at least some of excitation waveguides 604 include phase and/or amplitude controllers such that the excitation waveguides are operative for steering an illumination pattern around detection zone 414. As a result, a single fixed-location collection waveguide can be used to collect scattered/fluorescent light from the detection zone. In some cases, this affords a simpler detection scheme and/or enables the use of a single large and sensitive detector (e.g., an avalanche photodiode, photomultiplier tube, etc.) APD to detect output optical signals that are too weak to collect with a conventional detector array. By correlating the detected light with the direction of the steered illumination pattern, angular information is retained.

FIG. 17 depicts a picture of a conventional flow cytometer flow cell in accordance with the prior art. Flow cell 1700 includes cell body 1702, channel 1704, fluid port 1706, and lens 1708.

Channel 1704 is formed through the length of cell body 1702 such that it defines a long conduit for conveying fluid through detection zone 414. Detection zone 414 is defined by the position of lens 1708, which is integrated into the flow cell such that it focuses free-space excitation light into the detection zone and collects light (e.g., forward- and side-scattered light and fluorescence signals) from the detection zone.

FIGS. 18A-B depict a flow cytometry flow cell in accordance with a third alternative embodiment of the present invention. Flow cell 1800 represents embodiments of the present invention that have substantially the same form factor as prior-art flow cells, but afford improved optical system performance and simpler operation. Flow cell 1800 comprises cell body 1802, channel 1804, fluid port 1706, and optofluidic system 1806.

Cell body 1802 is analogous to cell body 1702; however cell body includes two conventional cell body portions 1702-1 and 1702-2, which are attached to either side of optofluidic system 1806. Typically, cell body portions 1702-1 and 1702-2 are joined with optofluidic system 1806 via a conventional joining technology, such as fusion bonding, glue, etc. Cell body portions 1702-1 and 1702-2 include sections of channel 1704, which bookend and fluidically couple flow channel 408 to collectively define channel 1804.

Optofluidic system 1806 is analogous to optics plate 404 and comprises plate 1808 and detection system 1812, which includes excitation network 1814, collection network 1816, and flow channel 408. Excitation network 1814 and collection network 1816 are analogous to excitation network 216 and collection network 218 and are formed in waveguide plane 1810, which is defined by the top surface of plate 1808.

It should be noted that the waveguides of excitation network 1814 and collection network 1816 are formed in the same waveguide plane. As a result, all of the excitation waveguides are arranged about one side of flow channel 408, while all of the collection waveguides are arranged about the other side of the flow channel. While the illumination pattern provided by such an arrangement is not as uniform as in some other embodiments of the present invention, it still typically represents a significant improvement over illumination patterns provided by prior-art flow cytometer arrangements (e.g., that shown of system 1700). In some embodiments, the waveguides of excitation network 1814 and collection network 1816 are disposed in two or more waveguide planes, as described above. Further, in some embodiments, the waveguides of excitation network 1814 and collection network 1816 are arranged in another arrangement about flow channel 408, such as those arrangements described above.

One skilled in the art will recognize that there are several ways to optically couple to and from excitation network 1814 and collection network 1816, such as butt coupling optical fibers to the waveguide networks, focusing free-space optical signals into the end facets of the networks, etc.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. An apparatus comprising:
   a substrate that defines a first plane, the substrate comprising a flow channel that is operative for conveying fluid along a first direction that is substantially orthogonal to the first plane, the flow channel being located within a first region of the substrate;
   a first surface waveguide that is optically coupled with the flow channel, the first surface waveguide being located in a second plane within the first region, wherein the second plane is substantially parallel with the first plane; and
   a second surface waveguide that is optically coupled with the flow channel in the first region, the second surface waveguide being located in a third plane within the first region, wherein the third plane is substantially parallel with the second plane;
   wherein the substrate, the first surface waveguide, and the second surface waveguide are monolithically integrated, and wherein the second plane is between the first plane and the third plane; and
   wherein the first surface waveguide is operatively coupled with a first phase controller that is operative for controlling the phase of a first light signal propagating in the first surface waveguide.

2. The apparatus of claim 1 further comprising a first layer that is disposed between a first core layer and a second core layer, wherein the first surface waveguide includes the first core layer and the first layer, and wherein the second surface waveguide includes the second core layer and the first layer, and further wherein the first layer is operative as a cladding layer in each of the first surface waveguide and second surface waveguide.

3. The apparatus of claim 1, further comprising:
   a first plurality of surface waveguides that includes the first surface waveguide, each of the first plurality of surface waveguides being located in the second plane in the first region and being optically coupled with the flow channel; and
   a second plurality of surface waveguides that includes the second surface waveguide, each of the second plurality of surface waveguides being located in the third plane in the first region and being optically coupled with the flow channel.

4. The apparatus of claim 3, wherein the first plurality of surface waveguides is arranged in a circular arrangement about the flow channel in the first region.

5. The apparatus of claim 4, wherein the second plurality of surface waveguides is arranged in a circular arrangement about the flow channel in the first region.

6. The apparatus of claim 3, wherein the first plurality of surface waveguides is arranged in a polygonal arrangement about the flow channel in the first region, the polygonal arrangement having a plurality of sides, each side including at least two surface waveguides of the first plurality thereof.

7. The apparatus of claim 6, wherein the second plurality of surface waveguides is arranged in a polygonal arrangement about the flow channel in the first region, the polygonal arrangement having a plurality of sides, each side including at least two surface waveguides of the second plurality thereof.

8. The apparatus of claim 1, wherein the second surface waveguide is operatively coupled with a second phase controller that is operative for controlling the phase of a second light signal propagating in the second surface waveguide.

9. The apparatus of claim 1, wherein the first phase controller comprises:
a surface waveguide core comprising a first material, the surface waveguide core being optically coupled with the first surface waveguide;
an upper cladding comprising a second material;
a first electrode;
a second electrode; and
a first layer comprising a piezoelectric material, the first layer being between the first electrode and second electrode;
wherein the first layer is operative for inducing a strain in the surface waveguide core when a voltage is applied between the first and second electrodes.

10. The apparatus of claim 9, wherein the piezoelectric material comprises lead zirconium titanate.

11. The apparatus of claim 9, wherein the substrate comprises fused silica.

12. An apparatus comprising:
a substrate having a thickness between a first major surface and a second major surface;
a first flow channel that is operative for conveying fluid through the thickness;
a first plurality of surface waveguides, each of the first plurality of surface waveguides being optically coupled with the flow channel in a first region, the first plurality of surface waveguides being coplanar in a first plane within the first region, wherein the first plurality of surface waveguides is arranged in a polygonal arrangement about the flow channel in the first region, the polygonal arrangement having a plurality of sides, each side including at least two surface waveguides of the first plurality thereof; and
a second plurality of surface waveguides, each of the second plurality of surface waveguides being optically coupled with the flow channel, the second plurality of surface waveguides being coplanar in a second plane within the first region;
wherein, the first major surface, the second major surface, the first plane, and the second plane are substantially parallel.

13. The apparatus of claim 12, wherein the first flow channel is operative for conveying the fluid along a first direction that is substantially orthogonal to the first major surface.

14. The apparatus of claim 12, wherein the first plurality of surface waveguides is operative for generating an optical pattern in the flow channel.

15. The apparatus of claim 14, wherein the first plurality of surface waveguides is operative for controlling the shape of the optical pattern.

16. The apparatus of claim 12, wherein at least one of the second plurality of surface waveguides is operatively coupled with a wavelength filter.

17. The apparatus of claim 12, wherein the first major surface is between the second major surface and each of the first plane and second plane.

18. The apparatus of claim 12, wherein the substrate, the first surface waveguide, and the second surface waveguide are monolithically integrated, and wherein the second plane is between the first plane and the third plane.

19. The apparatus of claim 12 further comprising a first phase controller, the first phase controller being optically coupled with a first surface waveguide of the first plurality thereof, the first phase controller being operative for controlling the phase of a first light signal propagating in the first surface waveguide.

20. The apparatus of claim 19, wherein the first phase controller comprises:
a surface waveguide core comprising a first material, the surface waveguide core being optically coupled with the first surface waveguide;
an upper cladding comprising a second material;
a first electrode;
a second electrode; and
a first layer comprising a piezoelectric material, the first layer being between the first electrode and second electrode;
wherein the first layer is operative for inducing a strain in the surface waveguide core when a voltage is applied between the first and second electrodes.

21. The apparatus of claim 20, wherein the piezoelectric material comprises lead zirconium titanate.

22. The apparatus of claim 20, wherein the substrate comprises fused silica.

23. A method comprising:
conveying a first fluid through a flow channel that is arranged along a first direction through a first region of a substrate having a thickness that is between a first major surface and a second major surface, wherein the substrate includes (1) a first plurality of surface waveguides that is coplanar in a first plane that is orthogonal to the first direction and (2) a second plurality of waveguides that is coplanar in a second plane that is parallel with the first plane, and wherein the first plurality of waveguides is arranged in a polygonal arrangement about the flow channel in the first region, the polygonal arrangement having a plurality of sides, each side including at least two surface waveguides of the first plurality thereof;
interrogating the first fluid with a first illumination pattern that is based on a first light signal emitted from a first surface waveguide of the first plurality thereof; and
coupling a first portion of the first illumination pattern into a second surface waveguide of the second plurality thereof, wherein the first portion is coupled into the second surface waveguide after the first illumination pattern has interacted with the first fluid, wherein the first surface waveguide, the second surface waveguide, and the substrate are monolithically integrated such that the first major surface is between the second major surface and each of the first plane and the second plane.

24. The method of claim 23 further comprising determining a characteristic of the first fluid based on the first portion.

25. The method of claim 23 further comprising:
providing a first plurality of light signals that includes the first light signal, wherein each of the first plurality of light signals is emitted by a different surface waveguide of the first plurality thereof;
wherein the first illumination pattern is based on the first plurality of light signals.

26. The method of claim 25 further comprising:
coupling a second portion of the first illumination pattern into a third surface waveguide that is included in the second plurality of surface waveguides, wherein the second portion is coupled into the third surface waveguide after the first illumination pattern has interacted with the first fluid.

27. The method of claim 25 further comprising controlling the shape of the illumination pattern by controlling the phase of at least one of the first plurality of light signals.

28. The method of claim 25 wherein the phase of the at least one of the first plurality of light signals is controlled by controlling a strain applied to at least one of the first plurality of surface waveguides.

29. The method of claim 28 wherein the strain is applied to the at least one of the first plurality of surface waveguides by providing a voltage differential across a first layer comprising a piezoelectric material, the first layer being operatively coupled with at least one of the first plurality of surface waveguides.

* * * * *